(12) United States Patent
Goodman et al.

(10) Patent No.: US 12,365,710 B2
(45) Date of Patent: Jul. 22, 2025

(54) HMGB1 PROTEIN DERIVATIVES FOR THE REMOVAL OF BIOFILMS

(71) Applicant: RESEARCH INSTITUTE AT NATIONWIDE CHILDREN'S HOSPITAL, Columbus, OH (US)

(72) Inventors: Steven David Goodman, Columbus, OH (US); Lauren Opremcak Bakaletz, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 1023 days.

(21) Appl. No.: 17/282,354

(22) PCT Filed: Oct. 4, 2019

(86) PCT No.: PCT/US2019/054851
§ 371 (c)(1),
(2) Date: Apr. 1, 2021

(87) PCT Pub. No.: WO2020/072993
PCT Pub. Date: Apr. 9, 2020

(65) Prior Publication Data
US 2021/0340198 A1 Nov. 4, 2021

Related U.S. Application Data

(60) Provisional application No. 62/742,102, filed on Oct. 5, 2018.

(51) Int. Cl.
*C07K 14/47* (2006.01)
*C07K 16/12* (2006.01)

(52) U.S. Cl.
CPC .......... *C07K 14/47* (2013.01); *C07K 16/1232* (2013.01); *C07K 2317/76* (2013.01)

(58) Field of Classification Search
CPC .................................................. C07K 14/47
See application file for complete search history.

(56) References Cited

U.S. PATENT DOCUMENTS

| | | | |
|---|---|---|---|
| 6,551,795 B1 | 4/2003 | Rubenfield et al. |
| 6,663,863 B2 | 12/2003 | Horvath et al. |
| 6,696,550 B2 | 2/2004 | Larosa et al. |
| 6,846,651 B2 | 1/2005 | Fleischmann et al. |
| 7,241,867 B2 | 7/2007 | Bakaletz et al. |
| 7,413,868 B2 | 8/2008 | Kauvar et al. |
| 7,638,282 B2 | 12/2009 | Bakaletz et al. |
| 7,811,591 B2 | 10/2010 | Bakaletz et al. |
| 7,816,086 B2 | 10/2010 | Bakaletz et al. |
| 7,939,344 B2 | 5/2011 | Kauvar et al. |
| 7,998,490 B2 | 8/2011 | Bakaletz et al. |
| 8,236,494 B2 | 8/2012 | Bakaletz et al. |
| 8,283,114 B2 | 10/2012 | Bakaletz et al. |
| 8,628,917 B2 | 1/2014 | Bakaletz et al. |
| 8,652,773 B2 | 2/2014 | Bakaletz et al. |
| 8,758,764 B2 | 6/2014 | Masignani et al. |
| 8,933,029 B2 | 1/2015 | Mcnicol et al. |
| 8,999,291 B2 | 4/2015 | Goodman et al. |
| 9,017,656 B2 | 4/2015 | Hancock et al. |
| 9,034,642 B2 | 5/2015 | Bakaletz et al. |
| 9,155,792 B2 | 10/2015 | Cottarel et al. |
| 9,745,366 B2 | 8/2017 | Goodman et al. |
| 10,570,193 B2 | 2/2020 | Kauvar et al. |
| 10,595,530 B2 | 3/2020 | Goodman et al. |
| 10,940,204 B2 | 3/2021 | Bakaletz et al. |
| 11,104,723 B2 | 8/2021 | Goodman et al. |
| 11,248,040 B2 | 2/2022 | Kauvar et al. |
| 11,497,780 B2 | 11/2022 | Goodman et al. |
| 11,746,136 B2 | 9/2023 | Goodman et al. |
| 2002/0132753 A1 | 9/2002 | Rosen et al. |
| 2003/0060410 A1 | 3/2003 | Tracey et al. |
| 2003/0099602 A1 | 5/2003 | Levin et al. |
| 2003/0229065 A1 | 12/2003 | Levy et al. |
| 2004/0202670 A1 | 10/2004 | Apicella |
| 2005/0049402 A1 | 3/2005 | Babcook et al. |
| 2005/0131222 A1 | 6/2005 | Fleischmann et al. |
| 2005/0221439 A1 | 10/2005 | Bakaletz et al. |
| 2006/0030539 A1 | 2/2006 | Nick et al. |
| 2006/0099207 A1 | 5/2006 | Wu et al. |
| 2006/0121047 A1 | 6/2006 | Tracey |
| 2006/0228384 A1 | 10/2006 | Eldridge |
| 2006/0240045 A1 | 10/2006 | Berthet et al. |
| 2007/0154529 A1 | 7/2007 | Bullerdiek |
| 2007/0207210 A1 | 9/2007 | Brown et al. |
| 2007/0264256 A1 | 11/2007 | Bakaletz et al. |
| 2007/0286822 A1 | 12/2007 | Sanders et al. |

(Continued)

FOREIGN PATENT DOCUMENTS

| | | |
|---|---|---|
| JP | 2005-519998 | 7/2005 |
| JP | 2006-506441 A | 2/2006 |

(Continued)

OTHER PUBLICATIONS

Blair et al., "The HMGB1 C-Terminal Tail Regulates DNA Bending", JMB, 2016, vol. 428, pp. 4060-4072.*
Starkova et al., "Structural Characteristics of High-Mobility Group Proteins HMGB1 and HMGB2 and Their Interaction with DNA" Int. J. Mol. Sci., 2023, 24, 3577.*
Ota et al., "Complete sequencing and characterization of 21,243 full-length human cDNAs", Nature Genetics, Jan. 2004, vol. 36, No., pp. 40-45.*
Park et al., "Redox State-Dependent Interaction of HMGB1 and Cisplatin-Modified DNA," Biochemistry, 2011, 50, pp. 2567-2574.

(Continued)

*Primary Examiner* — Suzanne M Noakes

(74) *Attorney, Agent, or Firm* — Foley & Lardner LLP

(57) ABSTRACT

Provided herein are derivatives of HMGB1 that have been engineered to possess the same efficacious anti-bio film activity but are smaller and do not induce inflammation.

11 Claims, 7 Drawing Sheets
Specification includes a Sequence Listing.

(56) References Cited

U.S. PATENT DOCUMENTS

| | | |
|---|---|---|
| 2009/0029929 A1 | 1/2009 | Nakajima et al. |
| 2009/0297555 A1 | 12/2009 | Kemble et al. |
| 2009/0324651 A1 | 12/2009 | Old et al. |
| 2010/0166771 A1 | 7/2010 | Bakaletz et al. |
| 2010/0291177 A1 | 11/2010 | Hermans et al. |
| 2010/0310569 A1 | 12/2010 | Bakaletz et al. |
| 2011/0135646 A1 | 6/2011 | Bakaletz et al. |
| 2011/0236306 A1 | 9/2011 | Goodman et al. |
| 2011/0293624 A1 | 12/2011 | Bakaletz et al. |
| 2012/0128701 A1 | 5/2012 | Goodman et al. |
| 2012/0148615 A1 | 6/2012 | Masignani et al. |
| 2013/0017204 A1 | 1/2013 | Bakaletz et al. |
| 2013/0078254 A1 | 3/2013 | Bakaletz et al. |
| 2013/0183323 A1 | 7/2013 | Wang |
| 2014/0120107 A1 | 5/2014 | Bakaletz et al. |
| 2014/0127221 A1 | 5/2014 | Bakaletz et al. |
| 2014/0287426 A1 | 9/2014 | Arnold et al. |
| 2014/0356389 A1 | 12/2014 | Masignani et al. |
| 2015/0010654 A1 | 1/2015 | Arnold et al. |
| 2015/0086542 A1 | 3/2015 | Goodman et al. |
| 2015/0086561 A1 | 3/2015 | Kauvar et al. |
| 2015/0110838 A1 | 4/2015 | Agrawal |
| 2015/0166641 A1 | 6/2015 | Goodman et al. |
| 2015/0197558 A1 | 7/2015 | Kauvar et al. |
| 2015/0216971 A1 | 8/2015 | Rotolo et al. |
| 2015/0218231 A1 | 8/2015 | Bakaletz et al. |
| 2015/0299298 A1 | 10/2015 | Kauvar et al. |
| 2015/0342848 A1 | 12/2015 | Bhushan et al. |
| 2016/0095316 A1 | 4/2016 | Goodman et al. |
| 2016/0175440 A1 | 6/2016 | Goodman et al. |
| 2016/0194384 A1 | 7/2016 | Goodman et al. |
| 2016/0237145 A1 | 8/2016 | Kauvar et al. |
| 2016/0244489 A1 | 8/2016 | Masignani et al. |
| 2016/0287630 A1 | 10/2016 | Wood et al. |
| 2016/0289278 A1 | 10/2016 | Bakaletz et al. |
| 2016/0340650 A1 | 11/2016 | Wagner et al. |
| 2017/0182205 A1 | 6/2017 | Zupancic et al. |
| 2017/0197028 A1 | 7/2017 | Goldsmith |
| 2017/0215417 A1 | 8/2017 | Bhushan et al. |
| 2018/0303900 A1 | 10/2018 | Bakaletz et al. |
| 2019/0000971 A1 | 1/2019 | Bakaletz et al. |
| 2019/0040127 A1 | 2/2019 | Wadehra et al. |
| 2019/0337996 A1 | 11/2019 | Bakaletz et al. |
| 2019/0338018 A1 | 11/2019 | Bakaletz et al. |
| 2020/0002409 A1 | 1/2020 | Goodman et al. |
| 2020/0190170 A1 | 6/2020 | Kauvar et al. |
| 2021/0100854 A1 | 4/2021 | Goodman et al. |
| 2021/0139551 A1 | 5/2021 | Goodman et al. |
| 2021/0139610 A1 | 5/2021 | Goodman et al. |
| 2021/0206841 A1 | 7/2021 | Goodman et al. |
| 2021/0228716 A1 | 7/2021 | Bakaletz et al. |

FOREIGN PATENT DOCUMENTS

| | | |
|---|---|---|
| JP | 2006-506467 | 2/2006 |
| JP | 2008-520552 | 6/2008 |
| JP | 2013-529893 | 7/2013 |
| JP | 2013-542185 A | 11/2013 |
| WO | WO-00/47104 A2 | 8/2000 |
| WO | WO-02/13826 A1 | 2/2002 |
| WO | WO-02/085295 | 10/2002 |
| WO | WO-03/026691 A1 | 4/2003 |
| WO | WO-03/026691 A2 | 4/2003 |
| WO | WO-2004/014418 A2 | 2/2004 |
| WO | WO-2004/044001 A2 | 5/2004 |
| WO | WO-2004/046345 A2 | 6/2004 |
| WO | WO-2004/072094 A2 | 8/2004 |
| WO | WO-2005/025604 A2 | 3/2005 |
| WO | WO-2005/111066 A2 | 11/2005 |
| WO | WO-2006/017816 A2 | 2/2006 |
| WO | WO-2006/083301 A2 | 8/2006 |
| WO | WO-2006/114805 A2 | 11/2006 |
| WO | WO-2006/138527 | 12/2006 |
| WO | WO-2007/001422 A2 | 1/2007 |
| WO | WO-2009/006699 A1 | 1/2009 |
| WO | WO-2011/123396 A1 | 10/2011 |
| WO | WO-2012/034090 A1 | 3/2012 |
| WO | WO-2012/151554 A1 | 11/2012 |
| WO | WO-2013/177596 A2 | 11/2013 |
| WO | WO-2014/016417 A1 | 1/2014 |
| WO | WO-2014/190096 A1 | 11/2014 |
| WO | WO-2014/201305 A1 | 12/2014 |
| WO | WO-2015/038339 A1 | 3/2015 |
| WO | WO-2015/048484 A2 | 4/2015 |
| WO | WO-2015/136311 A1 | 9/2015 |
| WO | WO-2016/154491 A1 | 9/2016 |
| WO | WO-2016/184795 A1 | 11/2016 |
| WO | WO-2017/023863 A1 | 2/2017 |
| WO | WO-2017/066719 A2 | 4/2017 |
| WO | WO-2017/192594 A1 | 11/2017 |
| WO | WO-2018/042385 A2 | 3/2018 |
| WO | WO-2018/050814 A1 | 3/2018 |
| WO | WO-2018/129092 A1 | 7/2018 |
| WO | WO-2018/170178 A1 | 9/2018 |
| WO | WO-2018/187615 A1 | 10/2018 |
| WO | WO-2020/006528 A2 | 1/2020 |
| WO | WO-2020/038963 A1 | 2/2020 |
| WO | WO-2020/072993 A1 | 4/2020 |
| WO | WO-2020/092554 A1 | 5/2020 |
| WO | WO-2021/007260 A2 | 1/2021 |

OTHER PUBLICATIONS

Stros et al., "A Role of Basic Residues and the Putative Intercalating Phenylalanine of the HMG-1 Box in DNA Supercoiling and Binding to Four-way DNA Junctions," The Journal of Biological Chemistry, vol. 275, No. 46, Aug. 8, 2000, pp. 35699-35707.

U.S. Appl. No. 14/885,800, filed Oct. 16, 2015, Goodman et al.

U.S. Appl. No. 15/078,987, filed Mar. 23, 2016, The Research Institute at Nationwide Children's Hospital.

U.S. Appl. No. 15/999,215, filed Aug. 16, 2018, Goodman et al.

U.S. Appl. No. 16/297,094, filed Mar. 8, 2019, Goodman et al.

U.S. Appl. No. 16/475,654, filed Jul. 2, 2019, Bakaletz et al.

U.S. Appl. No. 16/475,656, filed Jul. 2, 2019, Bakaletz et al.

U.S. Appl. No. 16/492,582, filed Sep. 9, 2019, Goodman et al.

U.S. Appl. No. 17/150,731, filed Jan. 15, 2021, The Research Institute at Nationwide Children's Hospital.

Adams et al., "D-158. Epitope-mapping the immune response of children with otitis media and adults with chronic obstructive pulmonary disease to the PilA protein of nontypeable Haemophilus influenzae type IV pilus," 107th General Meeting, American Society for Microbiology; Toronto, ON, 2007, 1 page.

Adams et al., "Epitope-mapping the immune response of children with otitis media and adults with chronic obstructive pulmonary disease to the PilA protein of nontypeable Haemophilus influenzae type IV pilus," Immunology, 9th International Symposium on Recent Advances in Otitis Media; St. Pete Beach, FL, 2007, p. 356, 1 page.

Andersson et al., "High Mobility Group 1 Protein (HMG-1) Stimulates Proinflammatory Cytokine Synthesis in Human Monocytes", The Journal of Experimental Medicine, vol. 192, No. 4, Aug. 21, 2000, pp. 565-570.

Andersson et al., "HMGB1 is a Therapeutic Target for Sterile Inflammation and Infection", Annual Review of Immunology, vol. 29, No. 1, Aug. 14, 2015, pp. 139-162.

Bakaletz et al., "Relative immunogenicity and efficacy of two synthetic chimeric peptides of fimbrin as vaccinogens against nasopharyngeal colonization by nontypeable Haemophilus influenzae in the chincilla," Vaccine, vol. 15, No. 9, 1997, pp. 955-961.

Bakaletz et al., "Protection against Development of Otitis Media Induced by Nontypeable Haemophilus influenzae by Both Active and Passive Immunization in a Chinchilla Model of Virus—Bacterium Superinfection," Infecion and Immunity, vol. 67, No. 6, Jun. 1999, pp. 2746-2762.

Barve et al., "Cloning and characterization of the mating type (MAT) locus from Ascochyta rabiei (teleomorph: Didymella rabiei) and a MAT phylogeny of legume-associated Ascochyta spp.," Fungal Genetics and Biology, vol. 39, No. 2, Feb. 10, 2003, pp. 151-167.

(56) References Cited

OTHER PUBLICATIONS

Bass, J.I.F et al. (2010) "Extracellular Dna: A Major Proinflammatory Component of *Pseudomonas aeruginosa* Biofilms," The Journal of Immunology 184:6386-6395.
Beech, I.B. et al. (2005) "Microbe-surface interactions in biofouling and biocorrosion processes," International Microbiology 8:157-168.
Brady, R.A. et al. (2006) "Identification of *Staphylococcus aureus* Proteins Recognized by the Antibody-Mediated Immune Response to a Biofilm Infection," Infection and Immunity 74(6):3415-3426.
Brandstetter et al., "Antibodies Directed Against Integration Host Factor Mediate Biofilm Clearance From Nasopore," The Laryngoscope, vol. 12, No. 11, Nov. 2013, pp. 2626-2632.
Brockson et al., "Evaluation of the kinetics and mechanism of action of anti-integration host factor—mediated disruption of bacterial biofilms," Molecular Microbiology, vol. 93, No. 6, Aug. 19, 2014, pp. 1246-1258, Supplementary Material, 6 pages.
Brockson et al., "Evaluation of the kinetics and mechanism of action of anti-integration host factor—mediated disruption of bacterial biofilms," Molecular Microbiology, vol. 93, No. 6, Aug. 19, 2014, pp. 1246-1258.
Brown et al., "Tolerance to Single, but Not Multiple, Amino Acid Replacements in Antibody VHCDR2", J. Immunol. May 1996, 155(9):3285-3291.
Catlin, "Extracellular Deoxyribonucleic Acid of Bacteria and a Deoxyribonuclease Inhibitor," Science, vol. 124, Sep. 7, 1956, pp. 441-442.
Ceri, H. et al. (1999) "The Calgary Biofilm Device: New Technology for Rapid Determination of Antibiotic Susceptibilities of Bacterial Biofilms," Journal of Clinical Microbiology 37(6):1771-1776.
Chen, C. et al. (2004) "Substrate specificity of Helicobacter pylori histone-like HU protein is determined by insufficient stabilization of DNA flexure points," Biochem J. 383:343-351.
Cho et al., "The modulation of the biological activities of mitochondrial histone Abf2p by yeast PKA and its possible role in the regulation of mitochondrial DNA content during glucose repression," Biochimica et Biophysica Acta, vol. 1522, No. 3, Oct. 4, 2001, pp. 175-186.
Coenye, T. et al. (2010) "In vitro and in vivo model systems to study microbial biofilm formation," Journal of Microbiological Methods 83:89-105.
Cohavy, O. et al. (1999) "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517.
Collarini, E.J. et al. (2009) "Potent High-Affinity Antibodies for Treatment and Prophylaxis of Respiratory Syncytial Virus Derived from B Cells of Infected Patients," J Immunol 183:6338-6345.
Dalai, B et al. (2009) "Histone-like protein H-NS regulates biofilm formation and virulence of Actinobacillus pheuropneumonia," Microbial Pathogenesis 46:128-134.
Darouiche, R.O. et al. (2004) "Treatment of Infections Associated with Surgical Implants," N Engl J Med 350:1422-1429.
Database Geneseq [Online] "Human high mobility group box-ABB (HMG-AB) protein, SEQ ID 29", Databased accession No. AGB07712, Jul. 26, 2007.
Devaraj et al., "DNABII proteins play a central role in UPEC biofilm structure", Molecular Microbiology, 2015, vol. 96, vol. 6, Jun. 2015, pp. 1119-1135.
Donlan, R.M. et al. (2002) "Biofilms: Survival Mechanisms of Clinically Relevant Microorganisms," Clinical Microbiology Reviews 15(2):167-193.
Durocher et al., "High-level and high-throughput recombinant protein production by transient transfection of suspension-growing human 293-EBNA1 cells," Nucleic Acids Research, vol. 30, No. 2, e9, Nov. 11, 2001, 9 pages.
E. Melloni, et al., "Extracellular release of the 'differentiation enhancing factor', a HMG 1 protein type, is an early step in murine erythroleukemia cell differentiation" FEBS Letters 368, Year 1995, pp. 466-470.
Eboigbodin, K.E. et al. (2008) "Characterization of the Extracellular Plymeric Substances Produced by *Escherichia coli* Using Infrared Spectroscopic, Proteomic, and Aggregation Studies," Biomacromolecules 9:686-695.
Estrela et al., "Combining Biofilm-Controlling Compounds and Antibiotics as a Promising New Way to Control Biofilm Infections", Pharamceuticals, vol. 3, No. 5, May 11, 2010, pp. 1374-1393.
Estrela et al., "Combining Biofilm-Controlling Compounds and Antibiotics as a Promising New Way to Control Biofilm Infections," Pharmaceuticals, vol. 3, May 11, 2010, pp. 1374-1393.
Extended European Search Report dated Aug. 1, 2022, from application No. 19868798.0.
Falciola et al., "Mutational analysis of the DNA binding domain A of chromosomal protein HMG1," Nucleic Acids Research, vol. 22, No. 3, Jan. 10, 1994, pp. 285-292.
Fan, Z. et al. (2002) "HMG2 Interacts with the Nucleosome Assembly Protein SET and is a Target of the Cytotoxic T-Lymphocyte Protease Granzyme A," Molecular and Cellular Biology 22(8):2810-2820.
Final Office Action in U.S. Appl. No. 14/493,051 dated Oct. 7, 2016, 6 pages.
Final Office Action in U.S. Appl. No. 14/535,254 dated Jun. 9, 2017, 6 pages.
Final Office Action in U.S. Appl. No. 14/885,800 dated May 4, 2017, 17 pages.
Final Office Action in U.S. Appl. No. 15/078,987 dated Dec. 28, 2016, 12 pages.
Final Office Action on U.S. Appl. No. 14/885,800 dated May 29, 2018, 24 pages.
Final Office Action on U.S. Appl. No. 14/967,228 dated Nov. 22, 2017, 26 pages.
Final Office Action on U.S. Appl. No. 13/073,782 dated Mar. 27, 2014, 8 pages.
Final Office Action on U.S. Appl. No. 13/229,575 dated Aug. 29, 2013, 17 pages.
Final Office Action on U.S. Appl. No. 13/229,575 dated Sep. 19, 2014, 34 pages.
Garcia-Contreras et al., "Protein Translation and Cell Death: The Role of Rare tRNAs in Biofilm Formation and in Activating Dormant Phage Killer Genes," PLoS ONE, vol. 3, No. 6, Jun. 11, 2008, e2394, 17 pages.
George et al., "Cystic fibrosis infections: treatment strategies and prospects," FEMS Microbiol Lett., vol. 300, Jun. 15, 2009, pp. 153-164.
Gerstel et al., "Complex Regulation of csgD Promoter Activity by Global Regulatory Proteins," Molecular Microbiology, vol. 49, No. 3, Aug. 2003, pp. 639-654.
Goldenberg et al., "Genetic and biochemical analysis of IHF/HU hybrid proteins", BioChimie, vol. 76, No. 10-11, Jan. 1, 1994, pp. 941-950.
Good et al., "Synthetic RNA silencing in bacteria—antimicrobial discovery and resistance breaking," Frontiers in Microbiology, vol. 2, No. 185, Sep. 12, 2011, pp. 1-11.
Goodman et al., "Biofilms can be dispersed by focusing the immune system on a common family of bacterial nucleoid-associated proteins", Advances in Mucosal Immunology, Jun. 29, 2011, pp. 1-13.
Goodman et al., "In Vitro Selection of Integration Host Factor Binding Sites," Journal of Bacteriology, vol. 181, No. 10, May 1999, pp. 3246-3255.
Goodman et al., "Replacement of Integration Host Factor Protein-induced DNA Bending by Flexible Regions of DNA," The Journal of Biological Chemistry, vol. 274, No. 52, Aug. 6, 1999, pp. 37004-37011.
Goshima et al., "Chimeric HU-IHF proteins that alter DNA-binding ability," Gene, vol. 118, No. 1, Sep. 1, 1992, pp. 97-102.
Govan et al., "Microbial pathogenesis in cystic fibrosis: mucoid Pseudomonas aeruginosa and Burkholderia cepacia," Microbiol. Rev., vol. 60, No. 3, Sep. 1996, pp. 539-574.
Granston et al., "Characterization of a Set of Integration Host Factor Mutants Deficient for DNA Binding," J. Mol. Biol., vol. 234, Jun. 21, 1993, pp. 45-59.
Greenspan et al., "Defining epitopes: It's not as easy as it seems," Nature Biotechnology, vol. 17, Oct. 1999, pp. 936-937.

(56) References Cited

OTHER PUBLICATIONS

Gustave et al., "Targeting bacterial integration host factor to disrupt biofilms associated with cystic fibrosis," Journal of Cystic Fibrosis, vol. 12, No. 4, Nov. 17, 2012, pp. 384-389.
Hall-Stoodley et al., "Bacterial Biofilms: From the Natural Environment to Infectious Diseases," Nature Reviews, Microbiology, vol. 2, Feb. 2004, pp. 95-108.
Hall-Stoodley et al., "Direct Detection of Bacterial Biofilms on the Middle-Ear *Mucosa* of Children With Chronic Otitis Media," JAMA, vol. 296, No. 2, Jun. 1, 2007, pp. 202-211.
Hall-Stoodley et al., "Evolving concepts in biofilm infections", Cellular Microbiology, vol. 11, No. 7, 2009, pp. 1034-1043.
Hall-Stoodley et al., "Characterization of biofilm matrix, degradation by DNase treatment and evidence of capsule downregulation in *Streptococcus pneumoniae* clinical isolates," BMC Microbiology, vol. 8, No. 173, Oct. 8, 2008, 16 pages.
Haluzi et al., "Genes Coding for Integration Host Factor Are Conserve in Gram-Negative Bacteria," Journal of Bacteriology, vol. 173, No. 19, Oct. 1991, pp. 6297-6299.
Harley et al., "The Molecular Action and Regulation of the Testis-Determining Factors, SRY (Sex-Determining Region on the Y Chromosome) and SOX9 [SRY-Related High-Mobility Group (HMG) Box 9]," Endocrine Reviews, vol. 24, No. 4, Aug. 2003, pp. 466-487.
Harriman, W.D. et al. (2008) "Antibody discovery via multiplexed single cell characterization," Journal of Immunological Methods 341:135-145.
Harrison, J.J. et al. (2010) "Microtiter susceptibility testing of microbes growing on peg lids: a miniaturized biofilm model for high-throughput screening," Nature Protocols 5(7):1236-1254.
Haruta et al., "A possible role of histone-like DNA-binding protein of *Streptococcus intermedius* in the pathogenesis of bile duct damage in primary biliary cirrhosis," Clinical Immunology, vol. 127, No. 2, Mar. 11, 2008, pp. 245-251.
Haruta et al., "Long-term bacterial exposure can trigger nonsuppurative destructive cholangitis associated with multifocal epithelial inflammation," Laboratory Investigation, vol. 90, Apr. 2010, pp. 577-588.
Hirotaka Kazama, et al., "Immune Tolerance Induction By Apoptotic Cells Requires Caspase—Dependent Oxidation of HMGB1", NIH Public Access, Immunity., Jul. 18, 2008, pp. 1-25.
Hoyle et al., "Bacterial Resistance to Antibiotics: The Role of Biofilms," Prog. Drug Res., vol. 37, 1991, pp. 91-105.
International Search Report and Written Opinion for PCT Application No. PCT/US2011/051107, mailed Jan. 25, 2012, 15 pages.
International Search Report and Written Opinion on PCT Application No. PCT/US2018/022508 dated Jul. 18, 2018, 17 pages.
International Search Report and Written Opinion on PCT Application No. PCT/US2019/054851 dated Feb. 28, 2020, 12 pages.
Janeway, "Manipulating the immune response to fight infection," Immunobiology: The Immune System in Health and Disease, 5th ed.; retrieved online from https://www.ncbi.nlm.nih.gov/books/NBK27131/, 2001, 13 pages.
Jodar et al., "Development of vaccines against meningococcal disease," Lancet, vol. 359, Apr. 27, 2002, pp. 1499-1508.
Johnson et al., "Chapter 8: Bending and Compaction of DNA by Proteins," Protein-Nucleic Acid Interactions: Structural Biology, 2008, pp. 176-220.
Jurcisek et al., "Role of Sialic Acid and Complex Carbohydrate Biosynthesis in Biofilm Formation by Nontypeable Haemophilus influenzae in the Chinchilla Middle Ear," Infection and Immunity, vol. 73, Jun. 2005, pp. 3210-3218.
Jurcisek et al., "Biofilms Formed by Nontypeable Haemophilus influenzae In Vivo Contain both Double-Stranded DNA and Type IV Pilin Protein," Journal of Bacteriology, vol. 189, No. 10, Feb. 15, 2007, pp. 3868-3875.
Kamashev et al., "The histone-like protein HU binds specifically to DNA recombination and repair intermediates," The EMBO Journal, vol. 19, No. 23, Oct. 13, 2000, pp. 6527-6535.

Kennedy et al., "Passive Transfer of Antiserum Specific for Immunogens Derived from a Nontypeable Haemophilus influenzae Adhesin and Lipoprotein D Prevents Otitis Media after Heterologous Challenge," Infection and Immunity, vol. 68, No. 5, May 2000, pp. 2756-2765.
Khrapunov, S. et al. (2006) "Binding then bending: A mechanism for wrapping DNA," PNAS 103(51):19217-19218.
Kim et al., "Proteins Released by Helicobacter pylori In Vitro," Journal of Bacteriology, vol. 184, No. 22, Nov. 2002, pp. 6155-6162.
Kirketerp-Moller et al., "Distribution, Organization, and Ecology of Bacteria in Chronic Wounds," Journal of Clinical Microbiology, vol. 46, No. 8, Aug. 2008, pp. 2717-2722.
Kornblit et al., "The genetic variation of the human HMG1 gene," Tissue Antigens, vol. 70, Apr. 12, 2007, pp. 151-156.
Kristian, S.A et al. (2003) "Alanylation of Teichoic Acids Protects *Staphylococcus aureus* against Toll-like Receptor 2-Dependent Host Defense in a Mouse Tissue Cage Infection Model," The Journal of Infectious Diseases 188:414-423.
Kyd et al., "Efficacy of the 26-Kilodalton Outer Membrane Protein and Two P5 Fimbrin-Derived Immunogens to Induce Clearance of Nontypeable Haemophilus influenzae from the Rat Middle Ear and Lungs as Well as from the Chinchilla Middle Ear and Nasopharynx," Infection and Immunity, vol. 71, No. 8, Aug. 2003, pp. 4691-4699.
Labbé et al., "Association of Smads with lymphoid enhancer binding factor 1/T cell-specific factor mediates cooperative signaling by the transforming growth factor-β and Wnt pathways," Proc. Natl. Acad. Sci. USA, vol. 97, No. 15, Jul. 18, 2000, pp. 8358-8363.
Lebeaux et al., "From in vitro to in vivo Models of Bacterial Biofilm-Related Infections," Pathogens, vol. 2, May 13, 2013, pp. 288-356.
Lee, H. et al. (2010) Analysis of nuclear high mobility group box I (HMGBI)-binding proteins in colon cancer cells: clustering with proteins involved in secretion and extranuclear function. J Proteome Res 9: 4661-70.
Li et al., "Retroviral cDNA Integration: Stimulation by HMG I Family Proteins," Journal of Virology, vol. 74, No. 23, Dec. 2000, pp. 10965-10974.
Liu et al., "The essentiality and involvement of *Streptococcus intermedius* histone-like DNA-binding protein in bacterial viability and normal growth," Molecular Microbiology, vol. 68, No. 5, Apr. 21, 2008, pp. 1268-1282.
Liu, D. et al. (2008) "Histone-like DNA binding protein of *Streptococcus intermedius* induces the expression of pro-inflammatory cytokines in human monocytes via activation of ERK1/2 and JNK pathways," Cellular Microbiology 10(1):262-276.
Lunsford et al., "DNA-Binding Activities in *Streptococcus gordonii*: Indentification of a Receptor-Nickase and a Histonelike Protein," Current Microbiology, vol. 32, 1996, pp. 95-100.
Lutz, H.U. et al. (1990) "Covalent binding of detergent-solubilized membrane glycoproteins to 'Chemobond' plates for ELISA," Journal of Immunological Methods 129:211-220.
M. Elizabeth Brockson et al., "Evaluation of the kinetics and mechanism of action anti-integration host factor-mediated disruption of bacterial biofilms: Anti-IHF-mediated biofilm collapse", Molecular Microbiology., Aug. 19, 2014, pp. 1-22.
Mann, E.E. et al. (2009) "Modulation of eDNA Release and Degradation Affects *Staphylococcus aureus* Biofilm Maturation," Plos One 4(6):e5822, 1-12.
Martinez-Antonio A et al. (2008), "Functional organization of *Escherichia coli* transcriptional regulatory network", J. Mol. Biol. vol. 381, p. 238-247.
Meluleni et al., (1995) "Mucoid Pseudomonas aeruginosa Growing in a Biofilm In Vitro are Killed by Opsonic Antibodies to the Mucoid Exopolysaccharide Capsule but Not by Antibodies Produced During Chronic Lung Infection in Cystic Fibrosis Patients," J. Immunology, 155:2029-2038.
Mo Freire, et al., "A Bacterial Biofilm Induced Oral Osteolytic Infection Can be Successfully Treated by Immuno-Targeting an Extracellular Nucleoid Associated Protein", Mol Oral Microbiol. Feb. 2017, p. 1-21.

(56) References Cited

OTHER PUBLICATIONS

Mouw et al., "Shaping the Borrelia burgdorferi genome: crystal structure and binding properties of the DNA-bending protein Hbb," Molecular Microbiology, vol. 63, No. 5, Jan. 22, 2007, pp. 1319-1330.
Mukherjee et al., "Quantitative protein expression and cell surface characteristics of *Escherichia coli* MG1655 biofilms," Proteomics, vol. 11, Nov. 1, 2010, pp. 339-351.
Murphy et al., "Microbial Interactions in the Respiratory Tract," The Pediatric Infectious Disease Journal, vol. 28, No. 10, Oct. 2009, pp. S121-S126.
Murphy, T.F. et al. (2002) "Biofilm formation by nontypeable Haemophilus influenzae: strain variablitiy, outer membrane antigen expression and role of pili," BMC Microbiology 2:7, 1-8.
Nakamura et al., "HMG Box A in HMG3 Protein Functions as a Mediator of DNA Structural Alteration Together with Box B," J. Biochem., vol. 129, No. 4, Feb. 5, 2001, pp. 643-651.
Nash et al., "Overproduction of *Escherichia coli* Integration Host Factor, a Protein with Nonidentical Subunits," Journal of Bacteriology, vol. 169, No. 9, Sep. 1987, pp. 4124-4127.
NCBI Gen Bank Accession No. ACE63256 (Apr. 1, 2009), 2 pages.
NCBI GenBank Accession No. BAA03950 (Feb. 16, 2008), 2 pages.
NCBI GenBank Accession No. CAA47740 (Nov. 11, 1998), 1 page.
NCBI GenBank Accession No. CAA49169 (Feb. 5, 2003), 2 pages.
NCBI Genebank: P0A6Y1 (Sep. 13, 2005), 7 pages.
Non-Final Office Action dated Oct. 13, 2021, from U.S. Appl. No. 16/492,582.
Non-Final Office Action for U.S. Appl. No. 14/493,051, mailed Oct. 8, 2015, 8 pages.
Non-Final Office Action for U.S. Appl. No. 14/493,051 dated Mar. 12, 2015, 8 pages.
Non-Final Office Action in U.S. Appl. No. 13/073,782, dated Jun. 10, 2013, 15 pages.
Non-Final Office Action in U.S. Appl. No. 14/493,051 dated Apr. 28, 2016, 7 pages.
Non-Final Office Action in U.S. Appl. No. 14/885,800 dated Oct. 31, 2016, 22 pages.
Non-Final Office Action in U.S. Appl. No. 15/078,987 dated Jul. 14, 2016, 15 pages.
Non-Final Office Action in U.S. Appl. No. 15/078,987 dated Jun. 14, 2017, 26 pages.
Non-Final Office Action in U.S. Appl. No. 15/078,987, mailed Mar. 16, 2018, 18 pages.
Non-Final Office Action in U.S. Appl. No. 13/073,782, dated Jun. 25, 2014, 5 pages.
Non-Final Office Action in U.S. Appl. No. 13/229,575, dated Jan. 10, 2013, 18 pages.
Non-Final Office Action in U.S. Appl. No. 13/229,575 dated Mar. 31, 2014, 32 pages.
Non-Final Office Action issued in U.S. Appl. No. 14/535,254 dated Mar. 25, 2016, 7 pages.
Non-Final Office Action on U.S. Appl. No. 14/493,051 dated Jan. 10, 2017, 4 pages.
Non-Final Office Action on U.S. Appl. No. 14/535,254 dated Jan. 26, 2018, 9 pages.
Non-Final Office Action on U.S. Appl. No. 14/535,254 dated Jul. 10, 2017, 5 pages.
Non-Final Office Action on U.S. Appl. No. 14/535,254 dated Sep. 9, 2015, 10 pages.
Non-Final Office Action on U.S. Appl. No. 14/885,800 dated Dec. 15, 2017, 16 pages.
Non-Final Office Action on U.S. Appl. No. 14/967,228 dated May 19, 2017, 21 pages.
Non-Final Office Action on U.S. Appl. No. 14/535,254 dated Aug. 12, 2016, 8 pages.
Non-Final Office Action on U.S. Appl. No. 14/885,800 dated Aug. 8, 2019, 9 pages.
Non-Final Office Action on U.S. Appl. No. 15/744,713 dated Nov. 8, 2019, 12 pages.

Notice of Allowability for U.S. Appl. No. 13/073,782 dated Mar. 4, 2015, 4 pages.
Notice of Allowance in U.S. Appl. No. 14/493,051 dated Apr. 25, 2017, 8 pages.
Notice of Allowance in U.S. Appl. No. 13/073,782, dated Aug. 19, 2014, 11 pages.
Notice of Allowance on U.S. Appl. No. 14/493,051 dated Jan. 27, 2017, 9 pages.
Notice of Allowance on U.S. Appl. No. 14/885,800 dated Nov. 13, 2019, 8 pages.
Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, pp. 279-289 (Dec. 10, 2009).
Novotny et al., "Structural Stability of Burkholderia cenocepacia Biofilms is Reliant on eDNA Structure and Presence of a Bacterial Nucleic Acid Binding Protein," Plos One, vol. 8, No. 6, e67629, Jun. 2013, 15 pages.
Novotny et al., "Detection and characterization of pediatric serum antibody to the Omp P5-homologous adhesin of nontypeable Haemophilus influenzae during acute otitis media," Vaccine, vol. 20, No. 29-30, Jun. 8, 2002, pp. 3590-3597.
Novotny et al., "Epitope mapping of the Outer Membrane Protein P5-Homologous Fimbrin Adhesin of Nontypeable Haemophilus influenzae," Infection and Immunity, vol. 68, No. 4, Apr. 2000, pp. 2119-2128.
Novotny et al., "Passive immunization with human anti-protein D antibodies induced by polysaccharide protein D conjugates protects chinchillas against otitis media after intranasal challenge with Haemophilus influenzae," Vaccine, vol. 24, No. 22, Mar. 27, 2006, pp. 4804-4811.
Novotny et al., "The Fourth Surface-Exposed Region of the Outer Membrane Protein P5-Homologous Adhesin of the Nontypable Haemophilus influenzae is an Immunodominant But Nonprotective Decoying Epitope," The Journal of Immunology, vol. 171, No. 4, Jun. 10, 2003, pp. 1978-1983.
Novotny, et al., "Kinetic analysis and evaluation of the mechanisms involved in the resolution of experimental nontypeable Haemophilus influenzae-induced otitis media after transcutaneous immunization", Vaccine 31, Jul. 25, 2013, pp. 3417-3426.
Novotny, et al., "Transcutaneous immunization as preventative and therapeutic regimens to protect against experimental otitis media due to nontypeable Haemophilus influenzae", Mucosal Immunol vol. 5 No. 1, Jul. 2011, pp. 456-467.
Novotny, et al., "Monoclonal antibodies against DNA-binding tips of DNABII proteins disrupt biofilms in vitro and induce bacterial clearance in vivo", EBioMedicine 10 (2016), pp. 33-44.
Oberto et al., "Histones, HMG, HU, IHF: Même combat," Biochimie, vol. 76, 1994, pp. 901-908.
Ordway et al., "Evaluation of Standard Chemotherapy in the Guinea Pig Model of *Tuberculosis*," Antimicrobial Agents and Chemotherapy, vol. 54, May 2010, pp. 1820-1833.
Orlova, V.V. et al., "A novel pathway of HMGB1-mediated inflammatory cell recruitment that requires Mac-1-integrin", EMBO J, vol. 26, No. 4, Year 2007, pp. 1129-1139.
Otto, "*Staphylococcus epidermidis*—the 'accidental' pathogen," Nature Reviews Microbiology, vol. 7, Aug. 2009, pp. 555-567.
Paull, T.T., Haykinson, M.J., and Johnson, R.C., "The nonspecific DNA-binding and -bending proteins HMG1 and HMG2 promote the assembly of complex nucleoprotein structures", Genes Dev 7, Year 1993, pp. 1521-1534.
PDB ID: 1IHF: Rice, P.A. et al. (1996), 1 page; retrieved online from http://www.rcsb.org/pdb/explore.do?structureId=IHF, 2 pages.
Pedulla et al., "A novel host factor for integration of mycobacteriophage L5," Proc. Natl. Acad. Sci. USA, vol. 93, Dec. 1996, pp. 15411-15416.
Penzo, M. et al., "Inhibitor of NF-kappa B kinases alpha and beta are both essential for high mobility group box 1-mediated chemotaxis", J Immunol 184, Apr. 15, 2010, pp. 4497-4509.
Percival, S.L. et al. (2015) "Biofilms and Wounds: An Overview of the Evidence," Advances in Wound Care 4(7):373-381.

(56) References Cited

OTHER PUBLICATIONS

Petersen et al., "Biofilm Mode of Growth of *Streptococcus intermedius* Favoreed by a Competence-Stimulating Signaling Peptide," Journal of Bacteriology, vol. 186, No. 18, Sep. 2004, pp. 6327-6331.

Pethe et al., "*Mycobacterium smegmatis* laminin-binding glycoprotein shares epitopes with *Mycobacterium tuberculosis* heparin-binding haemagglutinin," Molecular Microbiology, vol. 39, No. 1, 2001, pp. 89-99.

Pistoia, V. and Raffaghello, L., "Damage-associated molecular patterns (DAMPs) and mesenchymal stem cells: a matter of attraction and excitement", Eur J Immunol 41, Year 2011, pp. 1828-1831.

Prymula et al., "*Pneumococcal capsular* polysaccharides conjugated to protein D for prevention of acute otitis media caused by both *Streptococcus pneumoniae* and non-typable Haemophilus influenzae: a randomized double-blind efficacy study," Lancet, vol. 367, No. 9512, Mar. 4, 2006, pp. 740-748.

Ranzato, E., Patrone, M., Pedrazzi, M., and Burlando, B. (2009) HMGbl promotes scratch wound closure ofHaCaT keratinocytes via ERKI/2 activation. Mal Cell Biochem 332: 199-205.

Rice et al., "Crystal Structure of an IHF-DNA Complex: A Protein-Induced DNA U-Turn," Cell, vol. 87, No. 7, pp. 1295-1306 (Dec. 27, 1996).

Rudikoff et al., "Single amino acid substitution altering antigen-binding specificity," Proc. Natl. Acad. Sci. USA, vol. 79, No. 6, Mar. 1982, pp. 1979-1983.

Rui Kang1, et al., "HMGB1 in Health and Disease", Mol Aspects Med., Dec. 2014, pp. 1-226.

Sapi et al., "Characterization of Biofilm Formation by Borrelia burgdorferi In Vitro," PLOS One, vol. 7, No. 10, Oct. 2012, pp. 1-11.

Schwartz, K. et al. (2012) "Functional Amyloids Composed of Phenol Soluble Modulins Stabilize *Staphylococcus aureus* Biofilms," PLOS Pathogens 8:e1002744, 1-11.

Segall et al., "Architectural elements in nucleoprotein complexes: interchangeability of specific and non-specific DNA binding proteins," The EMBO Journal, vol. 13, No. 19, 1994, pp. 4536-4548.

Shahrooei et al., "Inhibition of *Staphylococcus epidermidis* Biofilm Formation by Rabbit Polyclonal Antibodies against the SesC Protein," Infection and Immunity, vol. 77, No. 9, Sep. 2009, pp. 3670-3678.

Singh et al., "Quorum-sensing signals indicate that cystic fibrosis lungs are infected with bacterial biofilms," Nature, vol. 407, No. 12, Oct. 12, 2000, pp. 762-764.

Skolnick, J. et al. (2000) "From genes to protein structure and function: novel applications of computational approaches in the genomic era," Trends in Biotechnology 18:34-39.

Smith et al., "Cystic Fibrosis Airway Epithelia Fail to Kill Bacteria Because of Abnormal Airway Surface Fluid," Cell, vol. 85, Apr. 19, 1996, pp. 229-236.

Stefania Mardente, et al., "HMGB1 induces the overexpression of miR-222 and miR-221 and increases growth and motility in papillary thyroid cancer cells", Oncology Reports, vol. 28, Jul. 9, 2012, pp. 2285-2289.

Stinson, M.W. et al. (1998) "*Streptococcal* Histone-Like Protein: Primary Structure of hlpA and Protein Binding to Lipoteichoic Acid and Epithelial Cells," Infection and Immunity 66(1):259-265.

Stoltz et al., "Cystic Fibrosis Pigs Develop Lung Disease and Exhibit Defective Bacterial Eradication at Birth," www.ScienceTranslationMedicine.org, vol. 2, No. 29, Apr. 28, 2010, pp. 1-8.

Stros et al., "The HMG-box: a versatile protein domain occurring in a wide variety of DNA-binding proteins," Cell. Mol. Life Sci., vol. 64, No. 19-20, Jun. 29, 2007, pp. 2590-2606.

Sun et al., "Inhibition of Biofilm Formation by Monoclonal Antibodies against *Staphylococcus epidermindis* RP62A Accumulation-Associated Protein," Clinical & Diagnostic Laboratory Immunology, vol. 12, No. 1, Jan. 2005, pp. 93-100.

Swinger et al., "IHF and HU: flexible architects of bent DNA," Current Opinion in Structural Biology, vol. 14, No. 1, 2004, pp. 28-35.

Takeda, "Polyhistidine Affinity Chromatography for Purification and Biochemical Analysis of Fungal Cell Wall-Degrading Enzymes," Affinity Chromatography, Dr. Sameh Magdeldin (Ed.), ISBN: 978-953-51-0325-7, In Tech, 2012, pp. 177-186.

Tang et al., "High Mobility Group Box 1 (HMGB1) Activates an Autophagic Response to Oxidative Stress", Antioxidants & Redox Signaling, vol. 15, No. 8, Oct. 15, 2011 (accepted Mar. 10, 2011), pp. 2185-2195.

Taudte et al., "Alanine mutagenesis of high-mobility-group-protein-1 box B (HMG1-B)," Biochem. J., vol. 347, Feb. 25, 2000, pp. 807-814.

Teter et al., "DNA Bending and Twisting Properties of Integration Host Factor Determined by DNA Cyclization," Plasmid, vol. 43, 2000, pp. 73-84.

Tetz et al., "Effect of DNase and Antibiotics on Biofilm Characteristics," Antimicrobial Agents and Chemotherapy, vol. 53, No. 3, Mar. 2009, pp. 1204-1209.

Thomas, "HMG1 and 2: architectural DNA-binding proteins," Biochemical Society Transactions, vol. 29, Pt. 4, Apr. 12, 2001, pp. 395-401.

US Final Office Action dated Apr. 8, 2022, from U.S. Appl. No. 16/492,582.

US Notice of Allowance dated Sep. 7, 2022, from U.S. Appl. No. 16/492,582.

Vajdos et al. "Comprehensive Functional Maps of the Antigen-binding Site of an Anti-ErbB2 Antibody Obtained with Shotgun Scanning Mutagenesis", J Mol. Biol., Jul. 5, 2002, 320(2), pp. 415-428.

Van Schaik et al., "DNA Binding: a Novel Function of *Pseudomonas aeruginosa* Type IV Pili," Journal of Bacteriology, vol. 187, No. 4, Feb. 2005, pp. 1455-1464.

Wang, H. et al. (1999) HMG-1 as a late mediator of endotoxin lethality in mice. Science 285, pp. 248-251.

Wei Gong, et al., "Amino acid residues 201-205 in C-terminal acidic tail region plays a crucial role in antibacterial activity of HMGB1", Journal of Biomedical Science, Sep. 14, 2009, pp. 1-10.

Whitchurch et al., "Extracellular DNA Required for Bacterial Biofilm Formation," Science, vol. 295, No. 5559, Feb. 22, 2002, p. 1487, 1 page.

Whitchurch et al., "Extracellular DNA Required for Bacterial Biofilm Formation," Science, vol. 295, No. 5559, Feb. 22, 2002, Supplementary Material, 2 pages.

Winters et al., "Isolation and Characterization of a *Streptococcus pyogenes* Protein that Binds to Basal Laminae of Human Cardiac Muscle," Infection and Immunity, vol. 61, No. 8, Aug. 1993, pp. 3259-3264.

Winther et al., "Location of Bacterial Biofilm in the Mucus Overlying the Adenoid by Light Microscopy," Head & Neck Surgery, vol. 135, No. 12, Dec. 2009, pp. 1239-1245.

Yang, D., Chen, Q., Yang, H., Tracey, K.J., Bustin, M., and Oppenheim, J.J., "High mobility group box-1 protein induces the migration and activation of human dendritic cells and acts as an alarmin", J Leukoc Biol 81, Jan. 2007, pp. 59-66.

Yang, H et al., "Redox modification of cysteine residues regulates the cytokine activity of high mobility group box-1 (HMGB1)", Mol Med 18, Year 2012, pp. 250-259.

Yoshida, M. (1996) Seikagaku Biochemistry 68(12):1829-1834.

Zetterstrom, C.K., Strand, M.L., and Soder, O., "The high mobility group box chromosomal protein 1 is expressed in the human and rat testis where it may function as an antibacterial factor", Hum Reprod 21, Year 2006, pp. 2801-2809.

Zimmerli et al., "Pathogenesis of Foreign Body Infection: Description and Characteristics of an Animal Model," The Journal of Infectious Diseases, vol. 146, No. 4, Oct. 1982, pp. 487-497.

Zimmerli, W. et al. (1984) "Pathogenesis of Foreign Body Infection," J. Clin. Invest. 73:1191-1200.

Zulianello et al., "The HimA and HimD subunits of integration host factor can specifically bind to DNA as homodimers," The EMBO Journal, vol. 13, No. 4, Apr. 1, 1994, pp. 1534-1540.

Yang, et al., "High Mobility Group Box Protein 1 (HMGB1): The Prototypical Endogenous Danger Molecule," Molecular Medicine, Oct. 27, 2015, Vo. 21, No. Supplement 1, pp. S6-S12.

(56) References Cited

OTHER PUBLICATIONS

Bakaletz et al., "New strategies to target bacterial biofilms", 28th Annual North American Cystic Fibrosis Conference (NACFC), Atlanta, GA, Oct. 9-11, 2014 (presentation), 2 pages.
Bjarnsholt, "The role of bacterial biofilms in chronic infections," APMIS (2013) 121(Suppl. 136):1-51.
Boles et al., "*Staphylococcal* biofilm disassembly," Trends in Microbiology (2011) 19(9):449-455.
Brinkmann et al., "Neutrophil extracellular traps kill bacteria", Science. 2004; 303(5663):1532-5. doi: 10.1126/science.1092385.
Chan, et al., "Growth-related changes in intracellular spermidine and its effect on efflux pump expression and quorum sensing in Burkholderia pseudomallei", Microbiology, vol. 156, No. 4, Apr. 1, 2010, pp. 1144-1154.
Chen et al., "Novel Strategies for the Prevention and Treatment of Biofilm Related Infections," Int. J. Mol. Sci., vol. 14, Sep. 6, 2013, pp. 18488-18501.
Chowdhury, et al., "DNA-Crosslinker Cisplatin Eradicates Bacterial Persister Cells", Biotechnology and Bioengineering, vol. 113, No. 9, Mar. 10, 2016, pp. 1984-1992.
Darvaj et al., "DNABII proteins play a central role in UPEC biofilm structure", Molecular microbiology. Jun. 2015. 96(6):1119-35, doi: 10.1111/mmi.12994. Epub Apr. 16, 2015.
De La Fuente-Nunez et al., "Broad-Spectrum Anti-biofilm Peptide That Targets a Cellular Stress Response," PLoS Pathog., vol. 10, No. 5, May 2014, pp. 1-12.
El-Halfawy, et al., "Chemical Communication of Antibiotic Resistance by a Highly Resistant Subpopulation of Bacterial Cells", Plos One, Jul. 3, 2013, vol. 8, No. 7, pp. e68874 (1-10).
Estelles et al., "A High-Affinity Native Human Antibody Disrupts Biofilm from *Staphylococcus aureus* Bacteria and Potentiates Antibiotic Efficacy in a Mouse Implant Infection Model," Antimicrobial Agents and Chemotherapy, vol. 60, No. 4, Apr. 2016, pp. 2292-2301.
Feng, et al., "Identification of new compounds with high activity against stationary phase Borrelia burgdorferi from the NCI compound collection", Emerging Microbes & Infections, vol. 4, Jun. 3, 2015, pp. 1-16.
Goodman et al., "Biofilms can be dispersed by focusing the immune system on a common family of bacterial nucleoid-associated proteins", Mucosal immunology. 2011; 4(6):625-37. Epub Jul. 1, 2011. doi: 10.1038/mi.2011.27.
Goodman, "A new immunotherapeutic approach that disperses biofilms, Banff Conference on Infectious Diseases", Banff, Alberta, Canada, May 18, 2012 (presentation), 9 pages.
Goodman, "Making and breaking biofilms", Ohio Branch American Society for Microbiology Annual Meeting, Columbus, OH, Apr. 11-12, 2014 (presentation), 12 pages.
Goodman, "Nucleoprotein complexes in the extracellular matrix are critical for the structural integrity of bacterial biofilms", 112th General Meeting, American Society for Microbiology, San Francisco, CA, Jun. 18, 2012 (presentation), 9 pages.
Goodman, "The DNABII family of proteins: Diagnostic markers and therapeutic targets of bacterial biofilms", International Congress on Bacteriology and Infectious Disease, Baltimore, MD, Nov. 21, 2013, 7 pages.
Gustave et al., Biofilms recovered from the sputum of CF patients contain the bacterial protein integration host factor (IHF), 25th Annual North American Cystic Fibrosis Conference, Anaheim, CA, Nov. 3-5, 2011 (poster), 1 page.
International Search Report and Written Opinion dated Feb. 4, 2022, from application No. PCT/US2021/040576, 24 pages.
John, et al., "Reversible Daptomycin Tolerance of Adherent Staphylococci in an Implant Infection Model," Antimicrobial Agents and Chemotherapy (2011) 55(7):3510-3516.
Joo, et al., "Molecular Basis of In Vivo Formation by Bacterial Pathogens," Chemistry & Biology (2012) 19:1503-1513.
Junkins, et al., "Autophagy Enhances Bacterial Clearance during *P. aeruginosa* Lung Infection", Plos One, vol. 8, No. 8, Aug. 28, 2013, pp. 1-13.

Justice et al., "Aberrant Community Architecture and Attenuated Persistence of Uropathogenic *Escherichia coli* in the Absence of Individual IHF Subunits," PLoS ONE, vol. 7, No. 10, Oct. 2012, pp. 1-11.
Kim et al., "Beta-Arm flexibility of HU from *Staphylococcus aureus* dictates the DNA-binding and recognition mechanism," Acta Cryst., D70, Oct. 30, 2014, pp. 3273-3289.
Kirino et al., "Effect of Unusual Polyamines on Cleavage of DNA by Restriction Enzymes," J. Biochem, 1990, vol. 107, pp. 661-665.
Lappann et al., "A dual role of extracellular DNA during biofilm formation of Neisseria meningitidis", Molecular microbiology. 2010; 75(6):1355-71. doi: 10.1111/j.1365-2958.2010.07054.x.
Liao, et al., "Enhancement of the antibiofilm activity of amphotericin B by polyamine biosynthesis inhibitors", International Journal of Antimicrobial Agents, vol. 46, Jul. 1, 2015, pp. 42-52.
Mahdi et al., "Holliday Junction Resolvases Encoded by Homologous rusA Genes in *Escherichia coli* K-12 and Phage 82", J. Mol. Biol., vol. 257, Jan. 19, 1996, pp. 561-573.
Malhotra et al., "Defining the functional epitopes of Integration Host Factor (IHF) to develop a novel biofilm-focused immunotherapeutic against nontypeable Haemophilus influenzae-induced chronic and recurrent otitis media", 18th International Symposium on Recent Advances in Otitis Media, National Harbor, MD, Jun. 7-11, 2015 (poster), 1 page.
Malhotra et al., "Fine mapping the functional epitopes within integration host factor, a novel therapeutic target for nontypeable Haemophilus influenza-induced diseases of the respiratory tract", Abst. 12th Annual AMA Research Symposium, Dallas, TX, Nov. 7, 2014, 1 page.
Malhotra et al., Identification of immunoprotective domains within the bacterial DNA-binding protein, integration host factor, 20th Annual Midwest Microbial Pathogenesis Meeting. The Ohio State University, Columbus, OH, Aug. 23-25, 2013 (poster), 1 page.
Malhotra et al., Identification of immunoprotective domains within the bacterial DNA-binding protein, integration host factor, Abst. Seventh Extraordinary International Symposium on Recent Advances in Otitis Media, Stockholm, Sweden, Jun. 12, 2013, 20 pages.
Malhotra et al., Identification of immunoprotective domains within the bacterial DNA-binding protein, integration host factor, Seventh Extraordinary International Symposium on Recent Advances in Otitis Media, Stockholm, Sweden, Jun. 15, 2013 (presentation).
Novotny et al., "Antibodies against the majority subunit of Type 1V pili disperse nontypeable Haemophilus influenza biofilms in a LuxS-dependent manner and confer therapeutics resolution of experimental otitis media," Mol. Microbiol., vol. 96, No. 2, Apr. 2015, pp. 1-32.
Novotny et al., "Structural stability of Burkholderia cenocepacia biofilms is reliant on eDNA structure and presence of a bacterial nucleic acid binding protein", PloS one. 2013; 8(6):e67629. Epub Jun. 27, 2013. doi: 10.1371/journal.pone.0067629.
Novotny, "Development of a novel biofilm-focused immunotherapeutic against NTHI-induced otitis media", 18th International Symposium on Recent Advances in Otitis Media, National Harbor, MD, Jun. 7-11, 2015 (presentation), 3 pages.
Novotny, et al., "Monoclonal antibodies against DNA-binding tips of DNABII proteins disrupt biofilms in vitro and induce bacterial clearance in vivo," 2016, EBioMedicine 10:33-44.
Novotny, et al., "Redirecting the immune response towards immunoprotective domains of a DNABII protein resolves experimental otitis media," npj Vaccines 4:43, Oct. 14, 2019, 12 pages.
Priyadarshini et al., "The nucleoid-associated protein HUβ affects global gene expression in Porphyromonas gingivalis", Microbiology. 2013; 159(Pt 2):219-29.First Published: Feb. 1, 2013.
Qu, et al., "Effects of norspermidine on Pseudomonas aeruginosa biofilm formation and eradication", MicrobiologyOpen, vol. 5, No. 3, Jan. 27, 2016, pp. 402-412.
Reffuveille et al., "A Broad-Spectrum Antibiofilm Peptide Enhances Antibiotic Action against Bacterial Biofilms", Antimicrobial Agents and Chemotherapy, vol. 58, No. 9, Sep. 2014, pp. 5363-5371.
Rocco et al. "Natural antigenic differences in the functionally equivalent extracellular DNABII proteins of bacterial biofilms

(56) References Cited

OTHER PUBLICATIONS provide a means for targeted biofilm therapeutics" Mol Oral Microbiol. Apr. 2017; 32(2):118-130. doi: 10.1111/omi.12157. First published: Mar. 14, 2016.

Rouviere-Yaniv et al., "Characterization of a novel, low-molecular-weight DNA-binding protein from *Escherichia coli*", Proceedings of the National Academy of Sciences of the United States of America. 1975; 72(9):3428-32. Epub Sep. 1, 1975.

Shields, R.C. et al. (2013) "Efficacy of a Marine Bacterial Nuclease against Biofilm Forming Microorganisms Isolated from Chronic Rhinosinusitis," PLoS ONE 8(2):e55339, 1-13.

Soyer-Gobillard, et al., "Location of B- and Z-DNA in the Chromosomes of a Primitive Eukaryote Dinoflagellate", The Journal of Cell Biology, vol. 111, No. 2, Aug. 1, 1990, pp. 293-308.

Thurnheer et al., "Colonisation of gingival epithelia by subgingival biofilms in vitro: role of 'red complex' bacteria," Archives in Oral Biology, vol. 59, No. 9, Sep. 2014, pp. 1-24.

Tjokro et al., "A biochemical analysis of the interaction of Porphyromonas gingivalis Hu PG0121 protein with DNA", PloS one. 2014; 9(3):e93266. Epub Apr. 1, 2014.

UniProtKB/TrEMBL A0A0E4BIL9. Putative DNA-binding protein HU (Sep. 16, 2015) [Retrieved from the Internet Jan. 12, 2017: <http://www.uniprot.org/uniprot/A0A0E4BIL9.txt?version=3>], 1 page.

Vanhelden, et al., "A new assay for anti-DNA antibodies in serum which includes the measurement of anti-Z-DNA", Clinical & Experimental Immunology, vol. 69, No. 2, Aug. 1987, pp. 394-402.

Woischnig et al., "High Affinity Native Human Monoclonal Antibody with Broad Cross-Species Biofilm Disrupting Activity", ICAAC, Sep. 20, 2015, 1 page.

Xiong et al., "A Human Biofilm-Disrupting Monoclonal Antibody Potentiates Antibiotic Efficacy in Rodent Models of both *Staphylococcus aureus* and *Acinetobacter baumannii* Infections," Antimicrob. Agents Chemother., vol. 61, No. 10, Oct. 2017, pp. 1-10.

Das et al., "Combined Action of Inhibitors of Polyamine Biosynthetic Pathway with a Known Antimalarial Drug Chloroquine on Plasmodium Falciparum," Pharmacological Research, 1995, vol. 13, No. 3/4, pp. 189-193.

Das et al., "Combined Action of Inhibitors or S-Adenosylmethionine Decarboxylase with an Antimalarial Drug, Chloroquine, on Plasmodium falciparum," J. Euk. Microbiol., 1997, vol. 44, No. 1, pp. 12-17.

Ding et al., "Autophagy Activation in Hepatocellular Carcinoma Contributes to the Tolerance of Oxaliplatin via Reactive Oxygen Species Modulation," Clinical Cancer Research, 2011, vol. 17, No. 19, pp. 6229-6238.

* cited by examiner

SEQUENCE LISTING

<160> NUMBER OF SEQ ID NOS: 16

<210> SEQ ID NO 1
<211> LENGTH: 215
<212> TYPE: PRT
<213> ORGANISM: Mus sp.

<400> SEQUENCE: 1

```
Met Gly Lys Gly Asp Pro Lys Lys Pro Arg Arg Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Glu Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Gly Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215
```

<210> SEQ ID NO 2
<211> LENGTH: 215
<212> TYPE: PRT
<213> ORGANISM: Homo sapiens

<400> SEQUENCE: 2

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
```

```
                  100                 105                 110
Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
        210                 215

<210> SEQ ID NO 3
<211> LENGTH: 87
<212> TYPE: PRT
<213> ORGANISM: Mus sp.

<400> SEQUENCE: 3

Lys Asp Pro Asn Ala Pro Lys Arg Pro Pro Ser Ala Phe Phe Leu Phe
1               5                   10                  15

Cys Ser Glu Tyr Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Glu Lys Leu Lys Glu
    50                  55                  60

Lys Tyr Glu Lys Asp Ile Ala Ala Tyr Arg Ala Lys Gly Lys Pro Asp
65                  70                  75                  80

Ala Ala Lys Lys Gly Val Val
            85

<210> SEQ ID NO 4
<211> LENGTH: 87
<212> TYPE: PRT
<213> ORGANISM: Homo sapiens

<400> SEQUENCE: 4

Lys Asp Pro Asn Ala Pro Lys Arg Pro Pro Ser Ala Phe Phe Leu Phe
1               5                   10                  15

Cys Ser Glu Tyr Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Ala Lys Leu Lys Glu
    50                  55                  60

Lys Tyr Glu Lys Asp Ile Ala Ala Tyr Arg Ala Lys Gly Lys Pro Asp
65                  70                  75                  80

Ala Ala Lys Lys Gly Val Val
            85

<210> SEQ ID NO 5
<211> LENGTH: 87
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 5

Lys Asp Pro Asn Ala Pro Lys Arg Pro Pro Ser Ala Phe Phe Leu Phe
1               5                   10                  15

Ser Ser Glu Tyr Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Glu Lys Leu Lys Glu
    50                  55                  60

Lys Tyr Glu Lys Asp Ile Ala Ala Tyr Arg Ala Lys Gly Lys Pro Asp
65                  70                  75                  80

Ala Ala Lys Lys Gly Val Val
                85

<210> SEQ ID NO 6
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Asp Pro Asn Ala Pro Lys Arg Pro Pro Ser Ala Phe Phe Leu Phe
1               5                   10                  15

Ser Ser Glu Tyr Arg Pro Lys Ile Lys Gly Glu His Pro Gly Leu Ser
            20                  25                  30

Ile Gly Asp Val Ala Lys Lys Leu Gly Glu Met Trp Asn Asn Thr Ala
        35                  40                  45

Ala Asp Asp Lys Gln Pro Tyr Glu Lys Lys Ala Ala Lys Leu Lys Glu
    50                  55                  60

Lys Tyr Glu Lys Asp Ile Ala Ala Tyr Arg Ala Lys Gly Lys Pro Asp
65                  70                  75                  80

Ala Ala Lys Lys Gly Val Val
                85

<210> SEQ ID NO 7
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Lys Gly Asp Pro Lys Lys Pro Arg Arg Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80
```

```
Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Glu Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

<210> SEQ ID NO 8
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

<210> SEQ ID NO 9
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Pro Lys Gly Glu Thr Lys Lys Phe Lys Asp Pro Asn Ala Pro
1               5                   10                  15

Lys Arg Pro Pro Ser Ala Phe Phe Leu Phe Cys Ser Glu Tyr Arg Pro
            20                  25                  30
```

Lys Ile Lys Gly Glu His Pro Gly Leu Ser Ile Gly Asp Val Ala Lys
            35                  40                  45

Lys Leu Gly Glu Met Trp Asn Asn Thr Ala Ala Asp Asp Lys Gln Pro
        50                  55                  60

Tyr Glu Lys Lys Ala Glu Lys Leu Lys Glu Lys Tyr Glu Lys Asp Ile
65                  70                  75                  80

Ala Ala Tyr Arg Ala Lys Gly Lys Pro Asp Ala Ala Lys Lys Gly Val
                85                  90                  95

Val

<210> SEQ ID NO 10
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Pro Pro Lys Gly Glu Thr Lys Lys Phe Lys Asp Pro Asn Ala Pro
1               5                   10                  15

Lys Arg Pro Pro Ser Ala Phe Phe Leu Phe Cys Ser Glu Tyr Arg Pro
                20                  25                  30

Lys Ile Lys Gly Glu His Pro Gly Leu Ser Ile Gly Asp Val Ala Lys
            35                  40                  45

Lys Leu Gly Glu Met Trp Asn Asn Thr Ala Ala Asp Asp Lys Gln Pro
        50                  55                  60

Tyr Glu Lys Lys Ala Ala Lys Leu Lys Glu Lys Tyr Glu Lys Asp Ile
65                  70                  75                  80

Ala Ala Tyr Arg Ala Lys Gly Lys Pro Asp Ala Ala Lys Lys Gly Val
                85                  90                  95

Val

<210> SEQ ID NO 11
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Pro Pro Lys Gly Glu Thr Lys Lys Phe Lys Asp Pro Asn Ala Pro
1               5                   10                  15

Lys Arg Pro Pro Ser Ala Phe Phe Leu Phe Ser Ser Glu Tyr Arg Pro
                20                  25                  30

Lys Ile Lys Gly Glu His Pro Gly Leu Ser Ile Gly Asp Val Ala Lys
            35                  40                  45

Lys Leu Gly Glu Met Trp Asn Asn Thr Ala Ala Asp Asp Lys Gln Pro
        50                  55                  60

Tyr Glu Lys Lys Ala Glu Lys Leu Lys Glu Lys Tyr Glu Lys Asp Ile
65                  70                  75                  80

Ala Ala Tyr Arg Ala Lys Gly Lys Pro Asp Ala Ala Lys Lys Gly Val
                85                  90                  95

Val

<210> SEQ ID NO 12

```
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Pro Pro Lys Gly Glu Thr Lys Lys Phe Lys Asp Pro Asn Ala Pro
1               5                   10                  15

Lys Arg Pro Pro Ser Ala Phe Phe Leu Phe Ser Ser Glu Tyr Arg Pro
                20                  25                  30

Lys Ile Lys Gly Glu His Pro Gly Leu Ser Ile Gly Asp Val Ala Lys
            35                  40                  45

Lys Leu Gly Glu Met Trp Asn Asn Thr Ala Ala Asp Asp Lys Gln Pro
50                  55                  60

Tyr Glu Lys Lys Ala Ala Lys Leu Lys Glu Lys Tyr Glu Lys Asp Ile
65                  70                  75                  80

Ala Ala Tyr Arg Ala Lys Gly Lys Pro Asp Ala Ala Lys Lys Gly Val
                85                  90                  95

Val

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Pro Lys Gly Glu Thr Lys Lys Lys Phe
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Pro Ser Leu Lys Leu
1               5

<210> SEQ ID NO 15
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Lys Gly Asp Pro Lys Lys Pro Arg Arg Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Cys Ser Glu Arg
            35                  40                  45

Trp Lys Thr Met Ser Ala Lys Glu Lys Gly Lys Phe Glu Asp Met Ala
50                  55                  60
```

-continued

```
Lys Ala Asp Lys Ala Arg Tyr Glu Arg Glu Met Lys Thr Tyr Ile Pro
 65                  70                  75                  80

Pro Lys Gly Glu Thr Lys Lys Lys Phe
                 85

<210> SEQ ID NO 16
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Lys Gly Asp Pro Lys Lys Pro Arg Gly Lys Met Ser Ser Tyr
  1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
                 35                  40                  45

Trp Lys Thr Met Ser Ala Lys Glu Lys Gly Lys Phe Glu Asp Met Ala
             50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe
                 85
```

HMGB1 PROTEIN DERIVATIVES FOR THE REMOVAL OF BIOFILMS

CROSS-REFERENCE TO RELATED APPLICATION

This application is a national stage application under 35 U.S.C. § 371 of PCT Application No. PCT/US2019/054851, filed Oct. 4, 2019, which in turn claims priority under 35 U.S.C. § 119(e) to U.S. Provisional Application Ser. No. 62/742,102, filed Oct. 5, 2018, the contents of each of which are hereby incorporated by reference in its entirety into the present disclosure.

STATEMENT OF FEDERAL SUPPORT

This invention was made with government support under Grant No. DC011818 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Apr. 1, 2021, is named 106887-7924 SL.txt and is 16,982 bytes in size.

FIELD OF THE DISCLOSURE

This invention generally relates to the methods and compositions to lessen and/or cure clinical or industrial bacterial biofilms.

BACKGROUND

Bacteria persisting in a biofilm in the human body cause about two-thirds of all chronic/recurrent diseases. These biofilms are comprised of bacteria protected by an outer "slime" that is often comprised primarily of DNA which prevents the innate and adaptive immune systems, antibiotics and other antibacterial agents from gaining access to the bacteria inside the biofilm. Biofilms make it extremely difficult to clear the infection from the body. Furthermore, biofilms can act as a reservoir for future acute infections often with lethal consequences.

At least one protein from the DNABII family of proteins is found in all known eubacteria and are naturally found outside of the bacterial cell. While they elicit a strong innate immune response, host subjects fail to naturally produce specific antibody to family members as a result of infection. The major problem with bacterial biofilms is the inability of the host immune system and/or antibiotics and other antimicrobials to gain access to the bacteria protected within the biofilm.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility to the point where fouling and corrosive biofilm organisms have even been found on the surfaces of final product storage tanks.

In the home, biofilms are found in or on any surface that supports microbial growth, e.g., in drains, on food preparation surfaces, in toilets and in swimming pools and spas.

Biofilms are implicated in a wide range of water processes, both domestic and industrial. They can grow on the surface of process equipment and impede the performance of the equipment, such as degradation of heat transfer or plugging of filters and membranes. Biofilms growing on cooling tower fill can add enough weight to cause collapse of the fill. Biofilms cause corrosion of even highly specialized stainless steels. Biofilms in a water process can degrade the value of a final product. Biofilms growing in drinking water distribution systems can harbor potential pathogenic organisms, corrosive organisms or bacteria that degrade the aesthetic quality of the water.

Thus, a need exists to break through the protective barrier of biofilms to treat or kill the associated bacterial infections and clear them from surfaces and in water systems. This disclosure satisfies this need and provides related advantages as well.

SUMMARY

Bacterial biofilms are notoriously recalcitrant to existing treatment modalities (for example they are >1000 fold more resistant to antimicrobials than their planktonic counterparts). Given the high prevalence and the enormous consequences in terms of attributable mortality and economic burden of biofilm-mediated infections, novel therapeutic approaches are urgently needed. One of the defining characteristics of a biofilm is the extracellular polymeric substance, in which biofilm cells are embedded. Key components of the extracellular polymeric substance are extracellular DNA and bacterial DNABII family of proteins, which are crucial to biofilms' structural integrity. Targeting and sequestration of DNABII proteins can disrupt biofilms. High Mobility Group B1 (HMGB1) protein is a DNA-binding eukaryotic protein that binds to the same DNA structures as the DNABII proteins, causing, disruption of bacterial biofilms. Derivatives of HMGB1 can be engineered to possess the same efficacious anti-biofilm activity but are smaller and do not induce inflammation.

Applicant discloses herein a new concept in the treatment of bacterial biofilm-mediated infections, by repurposing derivatives of an innate immune effector. HMGB1 domains are functionally different. Domain variants with anti-biofilm activities and no pro-inflammatory outcomes represent one embodiment of HMGB1 to treat biofilm-mediated infections without the consequences of excessive inflammation. In vivo and ex vivo experiments showed that antibodies against the DNABII family of bacterial nucleoid-associated proteins (IHF and HU) are highly effective against many different bacterial biofilms that cause a variety of recalcitrant human infections. In contrast, this disclosure utilizes HMGB1, an immune response component, to treat biofilm-mediated diseases without the consequence of excessive inflammation. In vitro bacterial biofilms were exposed to the anti-biofilm properties of HMGB1 and its various truncated domains (A box, B box, B box linker, mutated B box C106S, AB boxes and all with linkers).

The compositions and formulations containing the protein derivatives are useful in the treatment of recalcitrant or chronic or recurrent biofilm-mediated infections. The compositions are useful to treat resistant nosocomial infections (including indwelling medical device-related infections such as catheter- or prosthetic device-related infections, and chronic/recurrent infections such as ear infections and respiratory tract infections in cystic fibrosis patients). Additionally, they can be used in combination with established treatments (i.e antibiotics) as it has been shown that many bacteria released from biofilms are more susceptible to both host defenses and antimicrobial agents.

Thus, in one aspect, this disclosure provides an isolated A Box polypeptide, optionally comprising, or alternatively consisting essentially of, or yet consisting of, one or more amino acid mutations selected from K12, C23 and C45 (e.g. the native K or C modified to an amino acid from the group selected from serine, glycine, alanine, valine, isoleucine or threonine) or an equivalent thereof, the equivalent comprising one or more amino acid mutations selected from K12, C23 and C45 e.g. the native K or C modified to an amino acid from the group selected from serine, glycine, alanine, valine, isoleucine or threonine. In one aspect, the mutation is a C45S mutation. The A Box polypeptide may further comprise a linker or peptide sequence located at one or both termini. A non-limiting example is a polypeptide linker of the sequence PPKGETKKKF (SEQ ID NO: 13). When recombinantly produced, the B Box polypeptides can be partially or fully acetylated, oxidized or phosphorylated. In one aspect, the A Box polypeptide comprises, or consists essentially of, or yet further consists of amino acids 1 to 70 of wild-type HMGB1 polypeptide that optionally contains one or more mutations as identified above.

Also provided herein is an isolated B Box polypeptide, optionally comprising, or alternatively consisting essentially of, or yet consisting of a mutation at amino acid C106 (e.g. the native cysteine to an amino acid from the group selected from serine, glycine, alanine, valine, isoleucine or threonine), or an equivalent thereof comprising a mutation at amino acid C106 (e.g. the native cysteine to an amino acid from the group selected from serine, glycine, alanine, valine, isoleucine or threonine). In one aspect, the B Box polypeptide comprises, or consists essentially of, or yet further consists of amino acids about 80 to about 176, or about 88 to about 164, or about 89 to about 162, or yet further about 80 to about 164, of the HMGB1 polypeptide. Additional locations for modification of the wild-type HMGB1 B Box polypeptide are shown in FIG. 1C.

The B Box polypeptide may further comprise a linker or peptide sequence located at one or both termini. A non-limiting example is a polypeptide linker of the sequence PPKGETKKKF (SEQ ID NO: 13). When recombinantly produced, the disclosed B Box polypeptides can be partially or fully acetylated, oxidized or phosphorylated.

In a further aspect, provided herein is an isolated AB Box polypeptide, optionally comprising, or alternatively consisting essentially of, or yet consisting of, one or more amino acid mutations selected from K12, C23, C45, or C106 (e.g. the native K or C modified to an amino acid from the group selected from serine, glycine, alanine, valine, isoleucine or threonine) or an equivalent thereof comprising one or more amino acid mutations selected from K12, C23 and C45 (e.g. the native K or C modified to an amino acid from the group selected from serine, glycine, alanine, valine, isoleucine or threonine). In one aspect, the mutation is a C45S mutation. In another aspect, the polypeptide comprises a mutation at amino acid C106 (e.g. the native cysteine to an amino acid from the group selected from serine, glycine, alanine, valine, isoleucine or threonine), or an equivalent thereof comprising one or more amino acid mutations selected from K12, C23, C45 and a mutation at amino acid C106 (e.g. the native cysteine to an amino acid from the group selected from serine, glycine, alanine, valine, isoleucine or threonine). In one aspect the AB Box polypeptide and equivalents comprise C45S and C106S mutations. In one aspect, the AB Box polypeptide or its equivalent comprises, or consists essentially of, or yet further consists of amino acids 1 to 176, or 1 to 162, or yet further 1 to 164, of the wild type HMGB1 polypeptide, with the noted amino acid mutations.

In a yet further aspect, the isolated AB Box polypeptide of further comprises a linker polypeptide located linking the A Box polypeptide and the B Box polypeptide and in one aspect, a second linker linking the B Box and a C Box polypeptide. A non-limiting example is a polypeptide linker of the sequence PPKGETKKKF (SEQ ID NO: 13). When recombinantly produced, the AB or A, B and C Box polypeptides can be partially or fully acetylated, oxidized or phosphorylated. In one aspect, an isolated mutated HMGB1 polypeptide is provided with 1 or more amino acid substitutions as described herein, in the A and/or B box domains that can optionally be partially or fully acetylated, oxidized or phosphorylated.

In one aspect, the isolated polypeptides further comprise a detectable label.

Also provided herein is a recombinant polypeptide comprising, or alternatively consisting essentially of, or yet consisting of, one or more of the isolated polypeptides as described herein, further comprising at least one additional amino acid located at either or both termini.

This disclosure also provides an antibody that binds to, or was raised against a mutated polypeptide as described herein. The antibodies are useful as diagnostic and prognostic agents. Further provided one or more isolated polypeptides and/or antibodies as described herein and a carrier, such as a pharmaceutically acceptable carrier.

This disclosure also provides polynucleotides encoding the isolated polypeptide or antibody as described herein as well as their complements. In one aspect, the polynucleotides are detectably labeled. The polynucleotides can optionally be operatively linked to a promoter and/or enhancer for expression of the polynucleotide. Further provided is a method of recombinantly producing the polypeptides by expressing the polynucleotides in an appropriate expression system such as a host cell, and then producing and isolating the recombinantly produced polypeptides.

Yet further provided is a vector comprising, or alternatively consisting essentially of, or yet consisting of, a polynucleotide as described herein.

In another aspect, provided herein is an isolated host cell comprising one of more of a polypeptide, a polynucleotide, or a vector as described herein. Compositions comprising a carrier and one of more of a polypeptide, a polynucleotide, or a vector as described herein are further provided. In one aspect, the carrier is a pharmaceutically acceptable carrier.

The polypeptides and compositions comprising them have multiple uses. For example, the can be used in a method for inhibiting, competing or titrating the binding of a DNABII polypeptide or protein to a microbial DNA by contacting the DNABII polypeptide or protein or the microbial DNA with the polypeptide or composition as described herein. They also can be used in methods for inhibiting, preventing or breaking down a microbial biofilm by contacting the biofilm with the polypeptide or composition as described herein.

The polypeptide and compostions also can be used in methods of inhibiting, preventing or breaking down a biofilm in a subject or treating an infection or disease associated with the biofilm, by administering to the subject an effective amount of the composition or polypeptide as described herein.

The polypeptides and compositions can further be used in methods for inhibiting, preventing or treating a microbial infection that produces a biofilm in a subject, by administering to the subject an effective amount of the composition or polypeptide as described herein.

The methods can further comprise contacting or administering an effective amount of an an additional agent, such as an antimicrobial agent to treat the underlying infection.

The biofilms and infections that can be treated by these methods can be caused by bacterial infections, e.g., infections by ESKAPE pathogens, uropathogenic *Escherichia coli* (UPEC), *Klebsiella pneumonia, Burkholderia cenocepacia, S. epidermidis, Streptococcus agalactiae, Neisseria meningitidis*, Treponemes, *denticola, pallidum), Burkholderia cepacia, Burkholderia pseudomallei, Haemophilus influenzae* (nontypeable)(NTHI), *Moraxella catarrhalis, Streptococcus pneumoniae, Streptococcus pyogenes, Pseudomonas aeruginosa*, or *Mycobacterium tuberculosis*. Device related infections caused by biofilms include, for example, ventricular derivations, on contact lens, on endotracheal tubes, on prosthetic cardiac valves, pacemakers, and vascular grafts, on tissue fillers and breast implants, on peripheral vascular catheters, on urinary catheters, on orthopedic implants and prosthetic joints. Tissue-related infections that can be treated by the compositions and methods include for example, chronic otitis media, chronic sinusitis, chronic tonsillitis, dental plaque, chronic laryngitis, endocarditis, lung infections (infections upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP)), kidney stones, billary tract infections, urinary tract infections, *Burkholderia* infections, osteomyelitis, wounds of the epidermis and chronic wounds.

The subject can be a mammal such as a human, or an infant or a juvenile.

Yet further provided is a kit comprising, or alternatively consisting of, or yet further consisting of, an isolated polypeptide, antibody, polynucleotide, vector, host cell, or composition as described herein and instructions for use.

BRIEF DESCRIPTION OF THE FIGURES

(FIG. 1A) HMGB1 is comprised of 3 domains: A Box, B Box, and an acidic C tail. The A+B Boxes are primarily DNA binding domains (bracket), while the C tail mediates nuclear functions, transcription stimulation, and antibacterial activity. The AAs for each domain are indicated (left). C23 and C45 can form a disulfide bond, resulting in reduced DNA binding affinity and increased pro-inflammatory activity. C106 mediates pro-inflammatory activity via RLR4-MD2 binding. C106S mutation has been shown to the reduce pro-inflammatory response without loss of binding. (FIG. 1B) Left: IHF dimer bound to DNA. The β-ribbon arms of IHF penetrate the minor groove to bend DNA, wrapping the molecule around the N-terminal α-helices from the concave side. Right: 2 HMGB1 A Box domains bound to DNA; Mimics A Box and B Box binding in native HMGB1. α-helices bind the minor groove, bending the DNA molecule from the convex side. Modified from PDB 4QR9. Amino acid sequences of HMGB1 polypeptides, truncates, fusions and mutated versions are provided in the Sequence Listing, infra. (FIG. 1C) The HMGB1 B Box construct is comprised of an N- and C-terminal linker as well as two predicted α-helical regions with a flexible linker between. Multiple amino acids (AA) in B Box can be post-translationally modified (PTM, acetylation/methylation of Lys, glycosylation of Asn, phosphorylation or Tyr, oxidation of Cys. However, no B Box PTMs were present in >20% of the rHMGB1 or nHM observed peptides from LC-MS/MS analysis/s. (FIG. 1D) Truncations remove flexible linkers from N- and C-terminal ends as well as either of the two α-helical regions. The two minimal helical region truncations (AA 99-133, 138-164) are believed to maintain anti-biofilm activity.

(FIG. 5A) Full-length HMGB1 isoforms (200 nM unless otherwise indicated) added to UPEC, *B. cenocepacia*, NTHI, or ESKAPE pathogens. 800 nM rHMGB1 and 200 nM mHMGB1 were added for *S. aureus* (ESKAPE). 800 nM rHMGB1, 800 nM mHMGB1, or 3.3 µM of α-1HF$_{Ec}$ 1gG were added for *E. faecium* (ESKAPE) and were incubated for 1 h as opposed to 16 h to avoid potential degradation by *E. faecium* proteases. (FIG. 5B) Representative images of UPEC biofilms incubated with increasing concentrations of rHMGB1. (FIG. 5C) Individual domains of HMGB1 (200 nM) were tested for anti-biofilm activity as above (dotted line indicates control values). Bars represent the SEM. Statistical significance compared to control was assessed with unpaired t-tests, *P<0.05. HMGB1 and its variants but not the A Box were able to significantly disrupt established biofilms formed by high priority human pathogens. (FIGS. 5D-5E) HMGB1 and variants disrupt preformed *Klebsiella pneumoniae* biofilms. rHMGB1, HMGB1 C45S (mHMGB1), bovine HMGB1 (bHMGB1), B box, B Box C106S (mB Box), A Box, and A+B Box were added (200 nM) at 24 h to preformed *K. pneumoniae* biofilms. After 16 h of incubation, biofilms were stained with LIVE/DEAD®, then visualized via confocal laser scanning microscopy. Images were analyzed by COMSTAT to calculate average thickness and total biomass. Error bars represent the SEM. ***P<0.0001; ns=not significant. HMGB1 and its variants, but not the A Box, significantly disrupted established *K. pneumoniae* biofilms.

(FIG. 7A) Aggregates of *B. cenocepacia* were visible by fluorescence microscopy in lung sections probed with an α-*B. cenocepacia* antibody. For prevention, (FIG. 7B) bronchoalveolar lavage (BAL) collected 18 h post-inoculation (hpi) was analyzed for CFU. (FIG. 7C) Neutrophils in BAL were quantified by differential cell counting. (FIG. 7D) Lung tissue collected 72hpi was fixed, embedded, sectioned, and stained with hematoxylin & eosin (10× magnification). For treatment, 72hpi (FIG. 7E) CFUs were quantified in BAL. (FIG. 7F) Neutrophil recruitment was analyzed 24 h after intraperitoneal (i.p.) administration of HMGB1 valiants by fluorescence-activated cell sorting of peritoneal lavage stained with α-CD45, α-CD11b, and αLy-6G. (FIG. 7G) Serum TNF-α. was measured by ELISA in mice injected i.p. with 0.2 nmol HMGB1 valiants, 5 mg/kg LPS, or both. LoD: limit of detection. Bars represent SD. *P<0.05. HMGB1 treatment significantly decreased *B. cenocepacia* CFUs in lungs, HMGB1 Cys to Ser mutations eliminated pro-inflammatory activity and none of the HMGB1 variants induced sepsis.

(FIG. 10A) Sections of OCT-embedded mucosal biomass from an NTHI-infected chinchilla middle ear were co-labeled for HMGB1 and DNABII protein for immunofluorescence microscopy. Double stranded eDNA was labeled with DAPI (white). (FIG. 10B) CF sputum incubated with antibiofilm treatments (PBS, 1:10 rabbit a-1HF$_{Ec}$, serum, 100 U/ml Pulmozyme® (DNase), 1 mM rHMGB1) at 37° C. for 1 h and optical density of surrounding media was measured at 0 hour and 2 hour. DNABII proteins and HMGB1 are present in mucosal biofilms fanned in vivo but do not co-localize on eDNA. Exogenous HMGB1 can disrupt biofilms present in CF sputum.

DETAILED DESCRIPTION

Figures 1A, 1B:
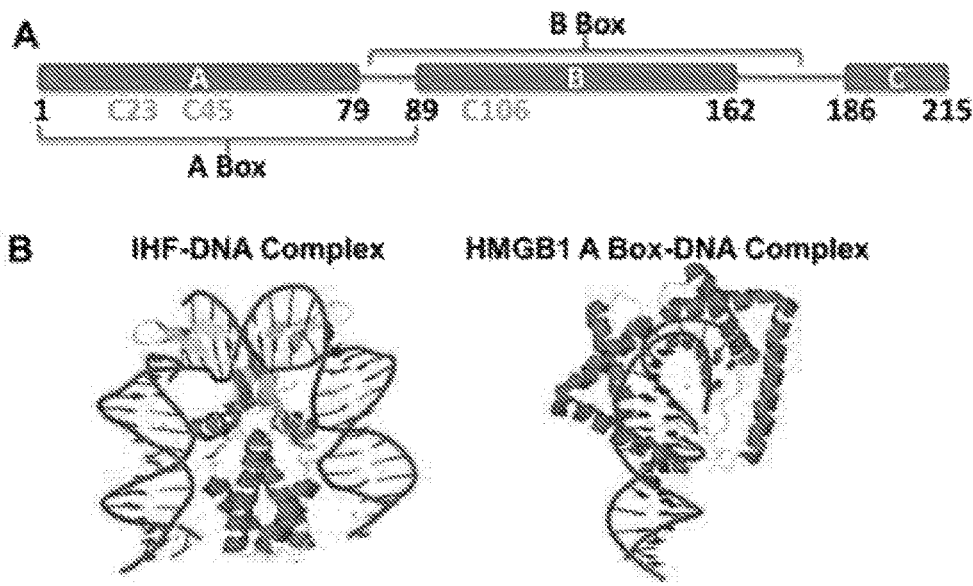
FIGS. 1A-1D: Structure of HMGB1, DNABII/HMGB1-DNA Complexes.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All technical and patent publications cited herein are incorporated herein by reference in their entirety. Nothing herein is to be construed as an admission that the disclosure is not entitled to antedate such disclosure by virtue of prior disclosure.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure. Embodiments defined by each of these transition terms are within the scope of this disclosure.

A "biofilm" intends a thin layer or an organized community of microorganisms that at times can adhere to the surface of a structure, that may be organic or inorganic, together with the polymers; such as DNA; that they secrete and/or release. The biofilms are very resistant to microbiotics and antimicrobial agents. They live on gingival tissues, teeth and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control estimate that over 65% of nosocomial (hospital-acquired) infections are caused by biofilms. Fungal biofilms also frequently contaminate medical devices. They cause chronic vaginal infections and lead to life-threatening systemic infections in people with hobbled immune systems. Biofilms also are involved in numerous diseases. For instance, cystic fibrosis patients have Pseudomonas infections that often result in antibiotic resistant biofilms.

A "DNABII polypeptide or protein" intends a DNA binding protein or polypeptide that is composed of DNA-binding domains and thus have a specific or general affinity for DNA. In one aspect, they bind DNA in the minor grove. Non-limiting examples of DNABII proteins are an integration host factor (IHF) protein and a histone-like protein from E. coli strain U93 (HU). Other DNA binding proteins that can be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813).

An "integration host factor" or "IHF" protein is a bacterial protein that is used by bacteriophages to incorporate their DNA into the host bacteria. These are DNA binding proteins that function in genetic recombination as well as in transcription and translational regulation. They also bind extracellular microbial DNA. The genes that encode the IHF protein subunits in E. coli are himA (Genbank accession No.: POA6X7.1) and himD (POA6Y1.1) genes. Homologs for these genes are found in other organisms, and peptides corresponding to these genes from other organisms can be found in Table 1.

"HMGB1" is a high mobility group box (HMGB) 1 protein that is reported to bind to and distort the minor groove of DNA and is an example of an interfering agent. Recombinant or isolated protein and polypeptide are commercially available from Atgenglobal, ProSpecBio, Protein1 and Abnova.

An "A Box" polypeptide intends a polypeptide comprising the A box domain of HMGB1 protein. The A Box polypeptide may be mutated or contain additional sequences such as a linker sequence, a signal sequence or a secretion sequence. Non-limiting examples are shown in the Figures and Sequence Listing. One or more point mutations in the amino acids K12, C23 and C45 can be introduced.

A "B Box" polypeptide intends a polypeptide comprising the B box domain of HMGB1 protein. The B Box polypeptide may be mutated or contain additional sequences such as a linker sequence, a signal sequence or a secretion sequence. A point mutations in the amino acid K114 or C106 can be introduced to effect DNA binding, inflammatory properties, and anti-biofilm activity. Non-limiting examples are shown in the Figures and Sequence Listing.

The "AB Box" polypeptide intends a polypeptide comprising the A and B box domains of HMGB1 protein fused together but absent amino acids that correspond to full length wild-type protein. The AB Box polypeptide may be mutated or contain additional sequences such as a linker sequence, a signal sequence or a secretion sequence. One or more point mutations in the amino acids as described herein (e.g., at amino acids K12, C23, C45, C106, and/or K114) can be introduced to effect DNA binding, inflammatory properties, and anti-biofilm activity. Non-limiting examples are shown in the Figures and Sequence Listing.

"HU" or "histone-like protein from E. coli strain U93" refers to a class of heterodimeric proteins typically associated with E. coli. HU proteins are known to bind DNA junctions. Related proteins have been isolated from other microorganisms. The complete amino acid sequence of E. coli HU was reported by Laine et al. (1980) Eur. J. Biochem. 103(3):447-481. Antibodies to the HU protein are commercially available from Abcam.

A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. Examples of peptide linkers is Gly-Pro-Ser-Leu-Lys-Leu (SEQ ID NO: 14) or PPKGETKKKF (SEQ ID NO: 13).

"Microbial DNA" intends single or double stranded DNA from a microorganism that produces a biofilm.

As used herein, the term "detectable label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this disclosure can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

As used herein the term "eDNA" refers to extracellular DNA found as a component to pathogenic biofilms.

As used herein, the ESKAPE pathogens include *Enterococcus faecium, Staphylococcus aureus, Klebsiella pneumoniae, Acinetobacter baumannii, Pseudomonas aeruginosa*, and *Enterobacter* species. These pathogens are the leading cause of nosocomial infections throughout the world.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, CA) and Promega Biotech (Madison, WI). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this disclosure. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this disclosure are other non-limiting techniques.

Figure 6:
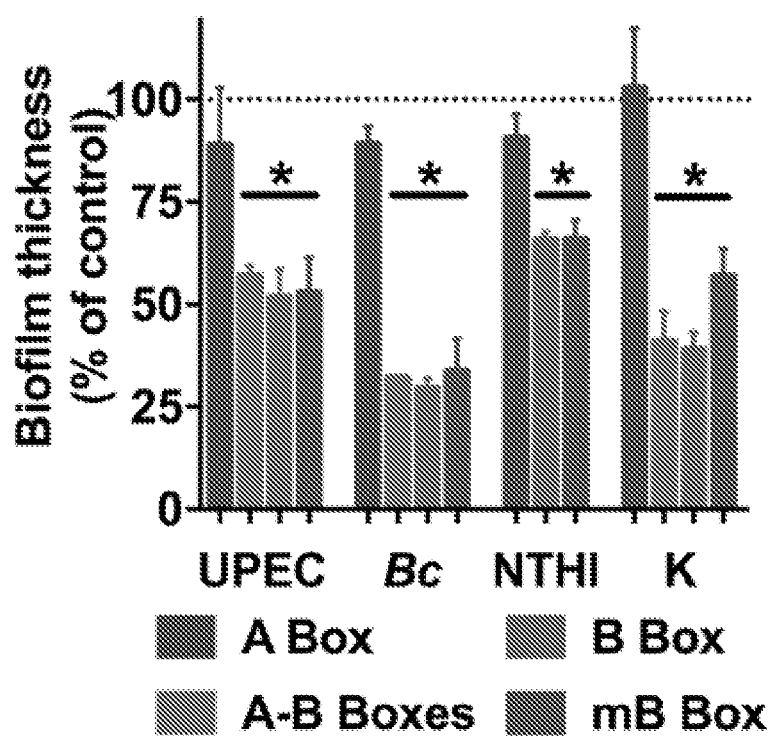
FIG. 6: HMGB1 variants disrupt pathogenic biofilms. Individual domains of HMGB1 (200 nM) were tested for anti-biofilm activity as above (dotted line indicates control values). Bars represent the SEM. *P<0.05. HMGB1 and its variants, but not the A Box, were able to significantly disrupt established biofilms formed by high priority human pathogens.

"Inhibiting, preventing or breaking down" a biofilm intends the prophylactic or therapeutic reduction in the structure of a biofilm. In one aspect, the terms "inhibiting, competing or titrating" intend a reduction in the formation of the DNA/protein matrix (for example as shown in FIG. 6) that is a component of a microbial biofilm. In one aspect, prevention is excluded from treatment.

A "bent polynucleotide" intends a double strand polynucleotide that contains a small loop on one strand which does not pair with the other strand and any polynucleotide where the end to end distance is reduced beyond natural thermal fluctuations i.e. that is bending beyond the persistence length of 150 bp for native B-form double stranded DNA. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9 or 10 bases.

A "subject" of diagnosis or treatment is a cell or an animal such as a mammal or a human. Non-human animals subject to diagnosis or treatment and are those subject to infections or animal models, for example, simians, murines, such as, rats, mice, chinchilla, canine, such as dogs, leporids, such as rabbits, livestock, sport animals and pets.

The term "protein", "peptide" and "polypeptide" are used interchangeably and in their broadest sense refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or alternatively about 80% homology or identity and alternatively, at least about 85%, or alternatively at least about 90%, or alternatively at least about 95% or alternatively 98% percent homology or identity and exhibits substantially equivalent biological activity to the reference protein, polypeptide or nucleic acid. In another aspect, the term intends a polynucleotide that hybridizes under conditions of high stringency to the reference polynucleotide or its complement.

A polynucleotide or polynucleotide region (or a polypeptide or polypeptide region) having a certain percentage (for example, 80%, 85%, 90% or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 30% identity or alternatively less than 25% identity, less than 20% identity, or alternatively less than 10% identity with one of the sequences of the present disclosure.

"Homology" or "identity" or "similarity" can also refer to two nucleic acid molecules that hybridize under stringent conditions to the reference polynucleotide or its complement.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, the terms "treating," "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder. In one aspect, "treatment" excludes prevention.

To "prevent" intends to prevent a disorder or effect in vitro or in vivo in a system or subject that is predisposed to the disorder or effect. An example of such is preventing the formation of a biofilm in a system that is infected with a microorganism known to produce one.

"Pharmaceutically acceptable carriers" refers to any diluents, excipients or carriers that may be used in the compositions of the disclosure. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, nasal administration, injection and topical application.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The agents and compositions can be used in the manufacture of medicaments and for the treatment of humans and other animals by administration in accordance with conventional procedures, such as an active ingredient in pharmaceutical compositions.

An agent of the present disclosure can be administered for therapy by any suitable route of administration. It will also be appreciated that the preferred route will vary with the condition and age of the recipient and the disease being treated.

An example of a solid phase support include glass, polystyrene, polypropylene, polyethylene, dextran, nylon, amylases, natural and modified celluloses, polyacrylamides, gabbros and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead or cylindrical, as in the inside surface of a test tube or the external surface of a rod. Alternatively, the surface may be flat such as a sheet, test strip, etc. or alternatively polystyrene beads. Those skilled in the art will know many other suitable carriers for binding antibody or antigen or will be able to ascertain the same by use of routine experimentation.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region or any portion thereof or at least one portion of a binding protein.

The antibodies can be polyclonal or monoclonal and can be isolated from any suitable biological source, e.g., murine, rat, sheep or canine.

"Immune response" broadly refers to the antigen-specific responses of lymphocytes to foreign substances. Any substance that can elicit an immune response is said to be "immunogenic" and is referred to as an "immunogen". All immunogens are antigens, however, not all antigens are immunogenic. An immune response of this disclosure can be humoral (via antibody activity) or cell-mediated (via T cell activation).

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

The term "modulate an immune response" includes inducing (increasing, eliciting) an immune response; and reducing (suppressing) an immune response. An immunomodulatory method (or protocol) is one that modulates an immune response in a subject.

An "HMG domain" or "high mobility group (HMG) box domain" refers to an amino acid sequence that is involved in binding DNA (Stros et al., Cell Mol Life Sci. 64(19-20): 2590-606 (2007)). In one embodiment, the structure of the HMG-box domain consists of three helices in an irregular array. In another embodiment, an HMG-box domain enables a protein to bind non-B-type DNA conformations (kinked or unwound) with high affinity. HMG-box domains can be found in high mobility group proteins, which are involved in the regulation of DNA-dependent processes such as transcription, replication and DNA repair, all of which require changing the conformation of chromatin (Thomas (2001) Biochem. Soc. Trans. 29(Pt 4):395-401).

Modes for Carrying Out the Disclosure

Polypeptide Compositions

Provided herein is a polypeptide comprising an HMG-box domain truncate and/or mutant as described herein, as well as proteins, fragments of these proteins that contain one or more of the HMG-box domain, truncate, mutant or equivalents of these proteins or fragments having the disclosed amino acid substitutions.

Thus, in one aspect, this disclosure provides an isolated A Box polypeptide, optionally comprising, or alternatively consisting essentially of, or yet consisting of, one or more amino acid mutations selected from K12, C23 and C45 (e.g. the native K or C modified to an amino acid from the group selected from serine, glycine, alanine, valine, isoleucine or threonine) or an equivalent thereof, the equivalent comprising one or more amino acid mutations selected from K12, C23 and C45, e.g. the native K or C modified to an amino acid from the group selected from serine, glycine, alanine, valine, isoleucine or threonine. In one aspect, the mutation is a C45S mutation. The A Box polypeptide may further comprise a linker or peptide sequence located at one or both termini. An examples of a peptide linker is PPKGETKKKF (SEQ ID NO: 13).

When recombinantly produced, the A Box polypeptides can be partially or fully acetylated, oxidized or phosphorylated, using methods known in the art, e.g., Olia A S, et al. (2015) ACS chemical biology. 10(9):2034-47. doi: 10.1021/acschembio.5b00342, PubMed PMID: 26083674; PubMed Central PMCID: PMC4610810; Ugrinova I, et al. (2102) Molecular Biology Reports, 2012; 39(11):9947-53. Epub 2012/06/29. doi: 10.1007/s11033-012-1863-x. PubMed PMID: 22740141; and Ito T, et al. (2007) JTH, 5(1):109-16. doi: 10.1111/j.1538-7836.2006.02255.x. PubMed PMID: 17239166. In one aspect, the A Box polypeptide comprises, or consists essentially of, or yet further consists of amino acids 1 to 70 of wild-type HMGB1 polypeptide, with the aforementioned mutations.

Examples of A Box polypeptides comprise, or consist essentially of, or yet further consist of:

```
                                          (SEQ ID NO: 15)
MGKGDPKKPR RKMSSYAFFV QTCREEHKKK HPDASVNFSE

FSKKCSERWK TMSAKEKGKF EDMAKADKAR YEREMKTYIP

PKGETKKKF (murine)

(SEQ ID NO: 16)
MGKGDPKKPR GKMSSYAFFV QTCREEHKKK HPDASVNFSE

FSKKCSERWK TMSAKEKGKF EDMAKADKAR YEREMKTYIP

PKGETKKKF (human)
```

As used herein, an equivalent of a polypeptide refers to a sequence that is at least about 70%, or alternatively at least about 75%, or at least about 80%, or at least about 85%, or at least about 90%, or at least about 95%, or at least about 98% or at least about 99% identical to the reference polypeptide that in one aspect, retain the mutated amino acid(s). In some aspects, the equivalent of a polypeptide retains the intended function and/or structural characteristics of the polypeptide, e.g., containing an HMG-box domain. In one aspect, the equivalent polypeptide includes a domain that is at least about 70%, or alternatively at least about 80%, or at least about 85%, or at least about 90%, or at least about 95%, or at least about 98% or at least about 99% identical to the HMG-box domain that in one aspect, retain the mutated amino acid(s). In some aspects, such an equivalent domain retains the function and/or structural characteristics of the HMB-box domain, e.g., binding to a HMB-box binding target. In one aspect, the equivalent polypeptide is encoded by a polynucleotide that can hybridize with a polynucleotide encoding the HMB-box domain polypeptide under stringent conditions.

Figures 1C, 1D:
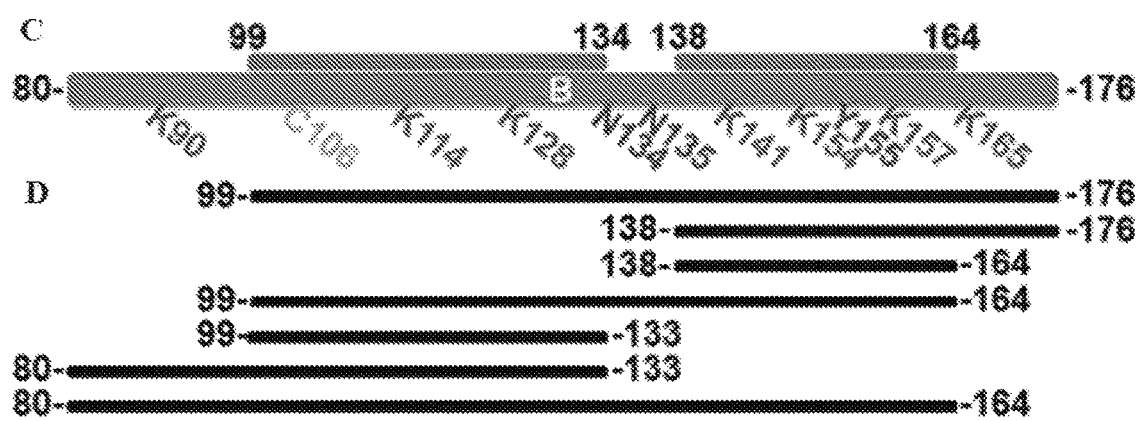

Also provided herein is an isolated B Box polypeptide, optionally comprising, or alternatively consisting essentially of, or yet consisting of a mutation at amino acid C106 or K114 (e.g. the native cysteine to an amino acid from the group selected from serine, glycine, alanine, valine, isoleucine or threonine, or an equivalent thereof comprising a mutation at amino acid C106 or K114 (e.g. the native cysteine to an amino acid from the group selected from serine, glycine, alanine, valine, isoleucine or threonine). In one aspect, the B Box polypeptide comprises, or consists essentially of, or yet further consists of amino acids about 80 to about 176, or about 88 to about 164, or about 89 to about 162, or yet further about 80 to about 164, of the wt HMGB1 polypeptide, with the aforementioned mutations. Additional locations for modification of the wild-type HMGB1 B Box polypeptide are shown in FIG. 1C. Examples of B Box polypeptides comprise, or consists essentially of, or yet further consist of:

```
                                          (SEQ ID NO: 3)
KDPNAPKRPPSAFFLFCSEYRPKIKGEHPGLSIGDVAKKLGEMWNNTAAD

DKQPYEKKAEKLKEKYEKDIAAYRAKGKPDAAKKGVV (murine)

(SEQ ID NO: 4)
KDPNAPKRPPSAFFLFCSEYRPKIKGEHPGLSIGDVAKKLGEMWNNTAAD

DKQPYEKKAAKLKEKYEKDIAAYRAKGKPDAAKKGVV (human)
```

The B Box polypeptide may further comprise a linker or peptide sequence located at one or both termini. An examples of a peptide linker is PPKGETKKKF (SEQ ID NO: 13). When recombinantly produced, the disclosed B Box polypeptides can be partially or fully acetylated, oxidized or phosphorylated, using methods known in the art, e.g., Olia A S, et al. (2015) ACS chemical biology. 10(9): 2034-47. doi: 10.1021/acschembio.5b00342, PubMed PMID: 26083674; PubMed Central PMCID: PMC4610810; Ugrinova I, et al. (2102) Molecular Biology Reports, 2012; 39(11):9947-53. Epub 2012/06/29. doi: 10.1007/s11033-012-1863-x. PubMed PMID: 22740141; and Ito T, et al. (2007) JTH, 5(1):109-16. doi: 10.1111/j.1538-7836.2006.02255.x. PubMed PMID: 17239166.

As used herein, an equivalent of a polypeptide refers to a sequence that is at least about 70%, or alternatively at least about 75%, or at least about 80%, or at least about 85%, or at least about 90%, or at least about 95%, or at least about 98% or at least about 99% identical to the reference polypeptide that in one aspect, retain the mutated amino acid(s). In some aspects, the equivalent of a polypeptide retains the intended function and/or structural characteristics of the polypeptide, e.g., containing an HMG-box domain. In one aspect, the equivalent polypeptide includes a domain that is at least about 70%, or alternatively at least about 80%, or at least about 85%, or at least about 90%, or at least about 95%, or at least about 98% or at least about 99% identical to the HMG-box domain that in one aspect, retain the mutated amino acid(s). In some aspects, such an equivalent domain retains the function and/or structural characteristics of the HMB-box domain, e.g., binding to a HMB-box binding target and optionally losing it pro-inflammatory response. In one aspect, the equivalent polypeptide is encoded by a polynucleotide that can hybridize with a polynucleotide encoding the HMB-box domain polypeptide under stringent conditions.

In a further aspect, provided herein is an isolated AB Box polypeptide, optionally comprising, or alternatively consisting essentially of, or yet consisting of, one or more amino acid mutations selected from K12, C23, C45; and C106 or K114 (e.g. the native K or C modified to an amino acid from the group selected from serine, glycine, alanine, valine, isoleucine or threonine) or an equivalent thereof comprising one or more amino acid mutations selected from K12, C23 and C45; and C106 or K114 (e.g. the native K or C modified to an amino acid from the group selected from serine, glycine, alanine, valine, isoleucine or threonine). In one aspect, the mutation is a C45S mutation. In another aspect, the polypeptide comprises a mutation at amino acid C106 (e.g. the native cysteine to an amino acid from the group selected from serine, glycine, alanine, valine, isoleucine or threonine), or an equivalent thereof comprising one or more amino acid mutations selected from K12, C23, C45 and a mutation at amino acid C106 (e.g. the native cysteine to an amino acid from the group selected from serine, glycine, alanine, valine, isoleucine or threonine). In one aspect the AB Box polypeptide comprises C45S and C106S mutations and equivalents retain these mutations. In one aspect, the AB Box polypeptide comprises, or consists essentially of, or yet further consists of amino acids 1 to 176, or 1 to 162, or yet further 1 to 164, of the wild type HMGB1 polypeptide, with the aforementioned mutations.

In a yet further aspect, the isolated AB Box polypeptide of further comprises a linker polypeptide located linking the A Box polypeptide and the B Box polypeptide and in one aspect, a second linker linking the B Box and a C Box polypeptide. When recombinantly produced, the AB or A, B and C Box polypeptides can be partially or fully acetylated, oxidized or phosphorylated. An examples of a peptide linker is PPKGETKKKF (SEQ ID NO: 13). In one aspect, an isolated mutated HMGB1 polypeptide is provided with 1 or more amino acid substitutions as described herein, in the A and/or B box domains that can optionally be partially or fully acetylated, oxidized or phosphorylated, using methods known in the art, e.g., Olia A S, et al. (2015) ACS chemical biology. 10(9):2034-47. doi: 10.1021/acschembio.5b00342, PubMed PMID: 26083674; PubMed Central PMCID: PMC4610810; Ugrinova I, et al. (2102) Molecular Biology Reports, 2012; 39(11):9947-53. Epub 2012/06/29. doi: 10.1007/s11033-012-1863-x. PubMed PMID: 22740141; and Ito T, et al. (2007) JTH, 5(1):109-16. doi: 10.1111/j.1538-7836.2006.02255.x. PubMed PMID: 17239166.

Example of a AB Box polypeptides comprise, or consists essentially of, or yet further consist of with the aforementioned mutations:

```
                                               (SEQ ID NO: 7)
MGKGDPKKPRRKMSSYAFFVQTCREEHKKKHPDASVNFSEFSKKCSERWK

TMSAKEKGKFEDMAKADKARYEREMKTYIPPKGETKKKFKDPNAPKRPPS

AFFLFCSEYRPKIKGEHPGLSIGDVAKKLGEMWNNTAADDKQPYEKKAEK

LKEKYEKDIAAYRAKGKPDAAKKGVV (murine)

(SEQ ID NO: 8)
MGKGDPKKPRGKMSSYAFFVQTCREEHKKKHPDASVNFSEFSKKCSERWK

TMSAKEKGKFEDMAKADKARYEREMKTYIPPKGETKKKFKDPNAPKRPPS

AFFLFCSEYRPKIKGEHPGLSIGDVAKKLGEMWNNTAADDKQPYEKKAAK

LKEKYEKDIAAYRAKGKPDAAKKGVV (human)
```

As used herein, an equivalent of a polypeptide refers to a sequence that is at least about 70%, or alternatively at least about 75%, or at least about 80%, or at least about 85%, or at least about 90%, or at least about 95%, or at least about 98% or at least about 99% identical to the reference polypeptide that in one aspect, retain the mutated amino acid(s). In some aspects, the equivalent of a polypeptide retains the intended function and/or structural characteristics of the polypeptide, e.g., containing an HMG-box domain. In one aspect, the equivalent polypeptide includes a domain that is at least about 70%, or alternatively at least about 80%, or at least about 85%, or at least about 90%, or at least about 95%, or at least about 98% or at least about 99% identical to the HMG-box domain that in one aspect, retain the mutated amino acid(s). In some aspects, such an equivalent domain retains the function and/or structural characteristics of the HMB-box domain, e.g., binding to a HMB-box binding target but does not induce a pro-inflammatory response. In one aspect, the equivalent polypeptide is encoded by a polynucleotide that can hybridize with a polynucleotide encoding the HMB-box domain polypeptide under stringent conditions.

In a further aspect, the isolated AB Box polypeptide further comprises a linker polypeptide located linking the A Box polypeptide and the B Box polypeptide.

Also provided is an isolated HMGB1 polypeptide comprising the A, B and C domains, wherein the polypeptide comprises, or consists essentially of, or yet further consists of, one or more amino acid mutations selected from K12, C23, C45, C106, or K114, or an equivalent thereof, the equivalent thereof comprising one or more amino acid mutations selected from K12, C23, C45, C106 or K114. As used herein, an equivalent of a polypeptide refers to a sequence that is at least about 70%, or alternatively at least about 75%, or at least about 80%, or at least about 85%, or at least about 90%, or at least about 95%, or at least about 98% or at least about 99% identical to the reference polypeptide that in one aspect, retain the mutated amino acid(s). In some aspects, the equivalent of a polypeptide retains the intended function and/or structural characteristics of the polypeptide, e.g., containing an HMG-box domain but does not induce a pro-inflammatory response. In one aspect, the equivalent polypeptide includes a domain that is at least about 70%, or alternatively at least about 80%, or at least about 85%, or at least about 90%, or at least about 95%, or at least about 98% or at least about 99% identical to the HMG-box domain that in one aspect, retain the mutated amino acid(s). In some aspects, such an equivalent domain retains the function and/or structural characteristics of the HMB-box domain, e.g., binding to a HMB-box binding target but does not induce a pro-inflammatory response. In one aspect, the equivalent polypeptide is encoded by a polynucleotide that can hybridize with a polynucleotide encoding the HMB-box domain polypeptide under stringent conditions.

In a further aspect, the isolated HMGB1 Box polypeptide further comprises linker polypeptides located linking the A Box polypeptide and the B Box polypeptide and a second linker polypeptide linking the B Box polypeptide and the C Box polypeptide. An examples of a peptide linker is PPKGETKKKF (SEQ ID NO: 13).

The polypeptides can be detectably labeled and/or combined with a carrier, e.g., a pharmaceutically acceptable carrier.

Antibodies and Derivatives Thereof

This disclosure also provides an antibody that binds and/or specifically recognizes and binds an isolated polypeptide for use in the methods disclosed herein. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof. In one aspect, the fragment comprises, or alternatively consists essentially of, or yet further consists of the CDR of the antibody. In one aspect, the antibody is detectably labeled or further comprises a detectable label conjugated to it. Also provided is a hybridoma cell line that produces a monoclonal antibody disclosed herein. Compositions comprising or alternatively consisting essentially of or yet further, consisting of one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and described herein.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses, e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest and then screened for the activity of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; and 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052; Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids or variable or constant regions from other isotypes.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180,370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Pat. Application Publication No. 2006/0211088; PCT International Application Publication No. WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments ($V_H$-$C_H1$-VH-$C_H1$) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677, 425) and amino acid mutations in the Fc hinge region to decrease the biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields, R. L. et al. (2002) J. Biol. Chem. 277:26733-26740; Umana et al. (1999) Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}I$, $^{131}I$ Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al. (1984) Anal. Biochem. 142:68-78); sulfhydryl groups (Koyama (1994) Chem. Abstr. 120:217-262) of amino acid residues and carbohydrate groups (Rodwell et al. (1986) PNAS USA 83:2632-2636; Quadri et al. (1993) Nucl. Med. Biol. 20:559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chloramhucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alphasarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins and mixed toxins.

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. 1994 Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995)).

Techniques for conjugating therapeutic agents to antibodies are well known (Amon et al. "Monoclonal Antibodies For Immunotargeting Of Drugs In Cancer Therapy," in Monoclonal Antibodies And Cancer Therapy; Reisfeld et al. (eds.), pp. 243-56 (Alan R. Liss, Inc. 1985); Hellstrom et al. "Antibodies For Drug Delivery," in Controlled Drug Delivery (2nd Ed.); Robinson et al. (eds.), pp. 623-53 (Marcel Dekker, Inc. 1987); Thorpe "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy," in Monoclonal Antibodies For Cancer Detection And Therapy, Baldwin et al. (eds.), pp. 303-16 (Academic Press 1985), and Thorpe et al. "The Preparation And Cytotoxic Properties Of Antibody-Toxin Conjugates," (1982) Immunol. Rev. 62:119-58).

The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or noncovalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohexane-I-carboxylate (sulfo-SMCC) (Karpovsky et al. (1984) J. Exp. Med. 160:1686; Liu et al. (1985) Proc. Natl. Acad. Sci. USA 82:8648). When the binding molecules are antibodies, they can be conjugated by sulfhydryl bonding of the C-terminus hinge regions of the two heavy chains.

The antibodies or fragments thereof of the present disclosure may be linked to a moiety that is toxic to a cell to which the antibody is bound to form "depleting" antibodies. These antibodies are particularly useful in applications where it is desired to deplete an NK cell.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab)'2, Fab', scF$_v$, and F$_v$.

In some of the aspects of the antibodies provided herein, the antibody comprises an Fc domain. In some of the aspects of the antibodies provided herein, the antibody is a non-human animal such as a rat, sheep, bovine, canine, feline or rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.
2) Amino acids with acidic side chains: aspartic acid, glutamic acid
3) Amino acids with uncharged polar side chains: asparagine, glutamine, serine, threonine, tyrosine.
4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

Polynucleotides, Vectors and Host Cells

This disclosure also provides isolated or recombinant polynucleotides encoding one or more of the above-identified polypeptides or antibodies and their respective complementary strands. Vectors comprising the isolated or recombinant polynucleotides are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, as well as termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides of the disclosure encode polypeptides, proteins, antibodies or fragments thereof having diagnostic and therapeutic utilities as described herein as well as probes to identify transcripts of the protein that may or may not be present. These nucleic acid fragments can by prepared, for example, by restriction enzyme digestion of larger polynucleotides and then labeled with a detectable marker. Alternatively, random fragments can be generated using nick translation of the molecule. For methodology for the preparation and labeling of such fragments, see Sambrook, et al. (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include prokaryotic and eukaryotic cells, e.g., mammalian cells, animal cells, human cells, simian cells, insect cells, yeast cells, and bacterial cells constructed using known methods. See Sambrook, et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g. a mammalian cell, an animal cell (rat or mouse), a human cell, or a prokaryotic cell such as a bacterial cell, containing a polynucleotide encoding a protein or polypeptide or antibody or fragment thereof.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

When the vectors are used for gene therapy in vivo or ex vivo, a pharmaceutically acceptable vector is preferred, such as a replication-incompetent retroviral or adenoviral vector. Pharmaceutically acceptable vectors containing the nucleic acids of this disclosure can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) BioTechniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides of this disclosure. The genetically modified cells can be produced by insertion of upstream regulatory sequences such as promoters or gene activators (see, U.S. Pat. No. 5,733,761).

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide of this disclosure under conditions permitting hybridization (preferably moderately stringent hybridization conditions) of complementary single-stranded polynucleotides, or more preferably, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al. (1989) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides of this disclosure can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (1994)) or MacPherson et al. (1991) and (1995), and references cited therein. Alternatively, one of skill in the art can use the sequences provided herein and a commercial DNA synthesizer to replicate the DNA. Accordingly, this disclosure also provides a process for obtaining the polynucleotides of this disclosure by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide of this disclosure are useful as hybridization probes or as an equivalent of the specific polynucleotides identified herein. Since the full coding sequence of the transcript is known, any portion of this sequence or homologous sequences, can be used in the methods of this disclosure.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned mRNA is at least about 80% identical to the homologous region. More preferably, the probe is 85% identical to the corresponding gene sequence after alignment of the homologous region; even more preferably, it exhibits 90% identity.

These probes can be used in radioassays (e.g. Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide of this disclosure. Accordingly, this disclosure also provides a probe comprising or corresponding to a polynucleotide of this disclosure, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally preferred, so as to increase stability and selectivity of the hybrid, and thereby improving the specificity of particular hybrid molecules obtained. More preferably, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively expression of the encoded polypeptide can be detected by various methods. In particular it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

In one aspect, the polypeptides comprising an HMG-box domain include wildtype and recombinantly produced polypeptides and proteins from prokaryotic and eukaryotic host cells.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody and standard techniques such as gel filtration, ion-exchange, reversed-phase and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, CA, USA. The synthesized polypeptide can be precipitated and further purified, for example by high performance liquid chromatography (HPLC). Accordingly, this disclosure also provides a process for chemically synthesizing the proteins of this disclosure by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using the host cell and vector systems described herein.

The polypeptides of this disclosure also can be combined with various solid phase carriers, such as an implant, a stent, a paste, a gel, a dental implant or a medical implant or liquid phase carriers, such as beads, sterile or aqueous solutions, pharmaceutically acceptable carriers, suspensions or emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of *E. coli*, mutant derivatives of cholera toxin, CPG oligonucleotides and adjuvants derived from squalene.

Therapeutic Methods

One embodiment of the present disclosure provides a method for inhibiting, competing or titrating the binding of a DNABII polypeptide or protein to a microbial DNA, comprising contacting the DNABII polypeptide or protein or the microbial DNA with a polypeptide as described herein, thereby inhibiting, competing or titrating the binding of the DNABII protein or polypeptide to the microbial DNA. In some aspects, the contacting is in vitro or in vivo.

Another embodiment of the present disclosure provides a method for inhibiting, preventing or breaking down a microbial biofilm, comprising contacting the biofilm with a polypeptide as described herein, thereby inhibiting, preventing or breaking down the microbial biofilm. In some aspects, the contacting is in vitro or in vivo.

Another embodiment of the present disclosure provides a method for disrupting a biofilm and clearance that does not enhance or induce an inflammatory response, comprising contacting the biofilm with a polypeptide comprising, or consisting essentially of, or consisting of a B Box polypeptide as described herein, thereby disrupting a biofilm and clearance that does not enhance or induce an inflammatory response. In some aspects, the contacting is in vitro or in vivo.

Yet another embodiment of the present disclosure provides a method of inhibiting, preventing or breaking down a biofilm in a subject, comprising administering to the subject an effective amount of a polypeptide as described herein, thereby inhibiting, preventing or breaking down the microbial biofilm. In one aspect, the method comprises, or consists essentially of, or yet further consists of administering an effective amount of a polypeptide comprising, or consisting essentially of, or consisting of a B Box polypeptide as disclosed herein.

Also provided, in another embodiment, is a method for inhibiting, preventing or treating a microbial infection that produces a biofilm in a subject, comprising administering to the subject an effective amount of a polypeptide as described herein, thereby inhibiting, preventing or treating a microbial infection that produces the biofilm in the subject. In one aspect, the method comprises, or consists essentially of, or yet further consists of administering an effective amount of a polypeptide comprising, or consisting essentially of, or consisting of a B Box polypeptide as disclosed herein.

In an aspect of any of the above embodiments, the polypeptide comprising, or alternatively consisting essentially of, or yet further consisting of an HMG-box domain is described as AB Boxes, A Box, and B Box, as well as mutants, truncates and fusion proteins as described herein (see FIG. 3) as well as equivalents thereof.

Figure 3:
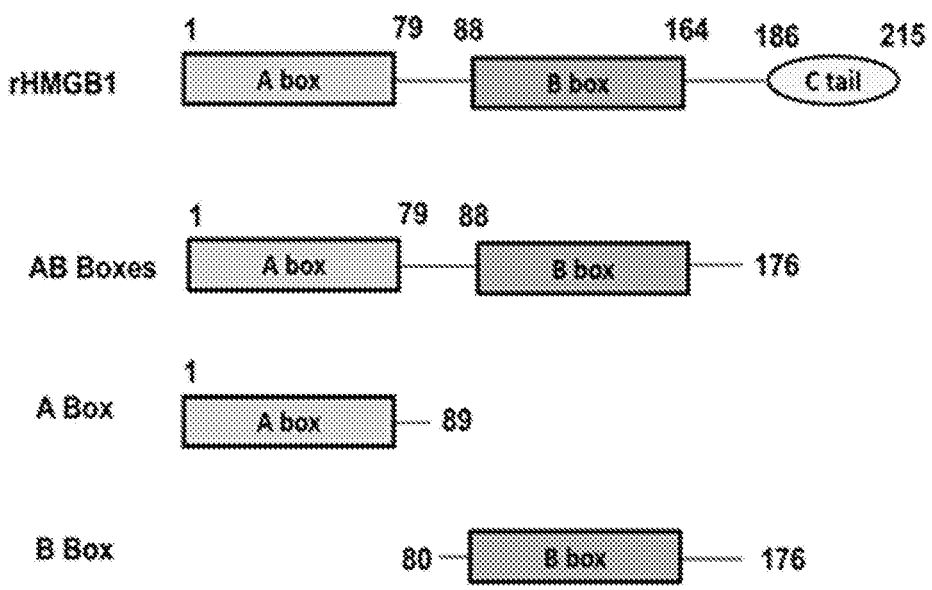
FIG. 3: Structure of HMGB1 and constructed variants. Full length recombinant HMGB1 (rHMGB1) expressed in *E. coli* contains 3 domains comprised of the A Box, B Box, and C tail. The HMGB1 AB Box construct is comprised of the A and B domains and the C terminal linker between the B box and C tail, but lacks the C tail. The A box construct contains the A box and the C-terminal linker between the between A and B boxes, but lacks the B-box and the C tail. The B box construct contains the N- and C-terminal linker but lacks the A Box and C tail. A C45S mutation in rHMGB1 (mHMGB1) and a C106S mutation in B Box (mB Box) was created to reduce the pro-inflammatory activities of HMGB1. See also FIG. 1.

Equivalents thereof comprise or alternatively consist essentially of, or yet further consist of, a polypeptide that is at least about 70%, or at least about 75%, or at least about 80%, or at least about 85%, or at least about 90%, or at least about 95%, or at least about 98% or at least about 99% identical to AB Boxes, A Box, and B Box, as well as mutants, truncates and fusions proteins as described herein (see FIG. 3). In some aspects, the equivalent retains the changed amino acid in the polypeptide, and retains the ability of the parent or reference protein, peptide, fusion or mutated version. In some aspect, the polypeptide comprising an HMG-box domain comprises or alternatively consists essentially of, or yet further consists of a biological equivalent to any polypeptide recited above.

In some aspects, the isolated or recombinant protein is a mammalian protein. In a particular aspect, the mammalian protein is a murine or a human protein. In a further aspect, the protein is a mammalian protein produced in an eukaryotic or a prokaryotic cell. They can be post-translationally modified using methods known in the art.

Any of the above method can further comprise or alternatively consists essentially of, or yet further consists of administering to the subject an effective amount of one or more of an antimicrobial, an antigenic peptide or an adjuvant. The subject, in one aspect, is a non-human animal or a human patient. In one aspect, the patient is a juvenile or an infant human.

The polypeptide is administered by a method comprising topically, transdermally, sublingually, rectally, vaginally, ocularly, subcutaneous, intramuscularly, intraperitoneally, urethrally, intranasally, by inhalation or orally.

In some aspects, the subject is a pediatric patient and the polypeptide is administered in a formulation for the pediatric patient.

In any of the above embodiments, the biofilm can comprise microbial DNA from a microorganism identified in Table 1.

Table 1. Examples of Bacterial Strains that can Generate Biofilms

*S. sobrinus*
*S. pyogenes*
*S. gordonii* Challis
*S. agalactiae*
*S. mutans*
*S. pneumoniae*
*S. gallolyticus*
*S. aureus*
*S. epidermidis*
*E. coli*
*H. influenza*
*Salmonella* enteric serovar *typhi*
*Aggregatibacter actinomycetemcomitans*
YP_003255304
*P. gingivalis*
*N. gonorrhoeae*
*N. meningitides*
NMB_1302
*P. aeruginosa*
*H. pylori*
*B. burgdorferi*
*Moraxella catarrhalis*
*V. cholera* El Tor
*Burkholderia cenocepacia*
*Burkholderia pseudomallei*
*Mycobacterium tuberculosis*
*Mycobacterium smegmatis*
*Treponema denticola*
*Treponema palladium* Nichols
*Prevotella melaninogenica*
*Prevotella intermedia*
*Bordetella pertusis* Tohama
*Enterococcus faecalis*

In one embodiment, the polypeptide is administered locally to the microbial infection and break down the biofilm.

In one embodiment, the present disclosure provides a method for inducing or providing an immune response in a subject in need thereof, comprising or alternatively consisting essentially of, or yet further consisting of administering to the subject an effective amount of a polypeptide as described herein. In another embodiment, the administration is local to where the immune response is desired. In one aspect, the method comprises, or consists essentially of, or yet further consists of administering an effective amount of a polypeptide comprising, or consisting essentially of, or consisting of a B Box polypeptide as disclosed herein. Examples of polypeptides comprising an HMG-box domain are described herein. In one aspect, the method comprises, or consists essentially of, or yet further consists of administering an effective amount of a polypeptide comprising, or consisting essentially of, or consisting of a B Box polypeptide as disclosed herein.

The isolated or recombinant protein can be a mammalian protein or in a particular aspect, a human protein. The subject, in some aspects, is a non-human animal or a human patient.

The agents and compositions of this disclosure can be concurrently or sequentially administered with other antimicrobial agents and/or surface antigens. In one particular aspect, administration is locally to the site of the infection. Other non-limiting examples of administration include by one or more method comprising transdermally, sublingually, rectally, vaginally, ocularly, subcutaneous, intramuscularly, intraperitoneally, intranasally, by inhalation or orally.

Also provided, in one embodiment, is the use of any of the above described polypeptides for the manufacture of a medicament in breaking down a biofilm or inhibiting, preventing or treating a microbial infection that produces a biofilm and providing the medical benefits described herein.

For some of these methods the contacting can be performed in vitro or in vivo. When the contacting is in vitro, the method provides a means to determine efficacy of the agents of this disclosure prior to animal or clinical studies and can be used to determine if the agents of this disclosure work synergistically with additional antimicrobials. When performed in vivo in an animal model, the method provides a means to determine efficacy of the agents of this disclosure prior to studies in human patients and can be used to determine if the agents of this disclosure work synergistically with additional antimicrobials.

Microbial infections and disease that can be treated by the methods of this disclosure include infection by the organisms identified in Table 1, e.g., *Streptococcus agalactiae, Neisseria meningitidis*, Treponemes, *denticola, pallidum, Burkholderia cepacia* or *Burkholderia pseudomallei*. In one aspect, the microbial infection is one or more of *Haemophilus influenzae* (nontypeable), *Moraxella catarrhalis, Streptococcus pneumoniae, Streptococcus pyogenes, Pseudomonas aeruginosa, Mycobacterium tuberculosis* and the ESKAPE pathogens. These microbial infections may be present in the upper, mid or lower airway (otitis, sinusitis or bronchitis) but also exacerbations of chronic obstructive pulmonary disease (COPD), chronic cough, complications of and/or primary cause of cystic fibrosis (CF) and community acquired pneumonia (CAP).

Infections might also occur in the oral cavity (caries, periodontitis) and caused by *Streptococcus mutans, Porphyromonas gingivalis, Aggregatibacter actinomycetemcomitans*. Infections might also be localized to the skin (abscesses, 'staph' infections, impetigo, secondary infection of burns, Lyme disease) and caused by *Staphylococcus aureus, Staphylococcus epidermidis, Pseudomonas aeruginosa* and *Borrelia burdorferi*. Infections of the urinary tract (UTI) can also be treated and are typically caused by *Escherichia coli*. Infections of the gastrointestinal tract (GI) (diarrhea, cholera, gall stones, gastric ulcers) are typically caused by *Salmonella enterica* serovar, *Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements or dental implants or medical devices such as pumps or monitoring systems, typically caused by a variety of bacteria, can be treated by the methods of this disclosure. These devices can be coated or conjugated to an agent as described herein.

Infections caused by *Streptococcus agalactiae* are the major cause of bacterial septicemia in newborns. Such infections can also be treated by the methods of this disclosure. Likewise, infections caused by *Neisseria meningitidis* which can cause meningitis can also be treated.

Thus, routes of administration applicable to the methods of the disclosure include intranasal, intramuscular, intratracheal, subcutaneous, intradermal, topical application, intravenous, rectal, nasal, oral and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In general, routes of administration suitable for the methods of the disclosure include, but are not limited to, enteral, parenteral or inhalational routes.

Parenteral routes of administration other than inhalation administration include, but are not limited to, topical, transdermal, subcutaneous, intramuscular, intraorbital, intracapsular, intraspinal, intrasternal and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The compounds of the disclosure can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods of the disclosure, the active will be administered orally on a continuous, daily basis, at least once per day (QD) and in various embodiments two (BID), three (TID) or even four times a day. Typically, the therapeutically effective daily dose will be at least about 1 mg, or at least about 10 mg, or at least about 100 mg or about 200—about 500 mg and sometimes, depending on the compound, up to as much as about 1 g to about 2.5 g.

Dosing of can be accomplished in accordance with the methods of the disclosure using capsules, tablets, oral suspension, suspension for intra-muscular injection, suspension for intravenous infusion, gel or cream for topical application or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments. In one aspect, the term "treatment" excludes prevention.

The compositions and related methods of the present disclosure may be used in combination with the administration of other therapies, or in the absence of such therapies. These include, but are not limited to, the administration of DNase enzymes, antibiotics, antimicrobials, or other antibodies. In one aspect, the polypeptide is administered with a DNase enzyme to treat a microbial infection and biofilm incident to cystic fibrosis.

In some embodiments, the methods and compositions include a deoxyribonuclease (DNase) enzyme that acts synergistically with a composition of this disclosure, e.g., a DNase. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current disclosure include minocycline, amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (e.g., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA, anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances, the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formulation or as a separate formulation.

Kits

Kits containing the agents and instructions necessary to perform the in vitro and in vivo methods as described herein also are claimed. Accordingly, the disclosure provides kits for performing these methods which may include a biological agent of this disclosure as well as instructions for carrying out the methods of this disclosure such as collecting tissue and/or performing the screen and/or analyzing the results and/or administration of an effective amount of biological agent as defined herein. These can be used alone or in combination with other suitable antimicrobial agents.

In one embodiment, the present disclosure provides a kit comprising a polypeptide as described herein and instructions for use in breaking down a biofilm or inhibiting, preventing or treating a microbial infection that produces a biofilm. In one embodiment, the kit further comprises one or more of an adjuvant, an antigenic peptide or an antimicrobial. In yet another embodiment, the kit further comprises a carrier selected from the group of a liquid carrier, a pharmaceutically acceptable carrier, a solid phase carrier, a pharmaceutically acceptable carrier, an implant, a stent, a paste, a gel, a dental implant or a medical implant.

The following examples are intended to illustrate, but not limit the disclosure.

Figure 2:
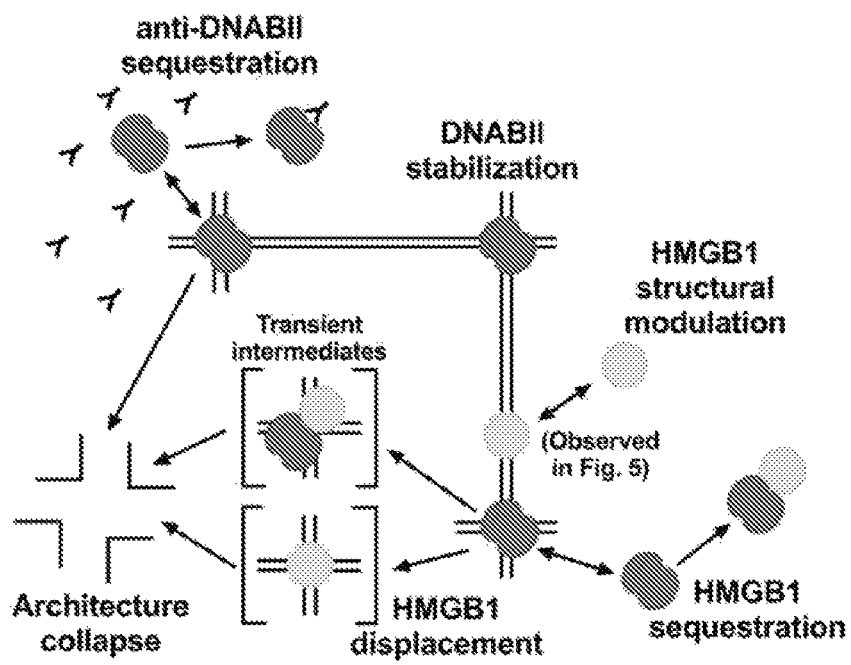
FIG. 2: Model of HMGB1-mediated biofilm collapse. DNABII proteins stabilize eDNA scaffolds via binding to vertex structures that resemble Holliday junctions (HJs). Antibodies (Y) can sequester DNABII proteins and shift the dynamic equilibrium, leading to collapse. HMGB1 can also destabilize eDNA structure via binding DNA and forming a transient, unstable intermediate (brackets).

Bacterial biofilm-mediated infections represent about 80% of all chronic/recurrent human infections. Biofilms constitute a protected mode of microbial growth. Namely, they are comprised of microbial communities attached to surfaces and embedded in a hydrated polymeric matrix of their own synthesis. Formation of these sessile communities allows bacterial survival in hostile environment making them, inherently resistant to conventional treatment modalities including antimicrobial agents and host defenses. Biofilm related infections are highly prevalent and related to notorious consequences in terms of attributable mortality and economic burden, thus making the need of novel therapeutic approaches urgent. In this regard, Applicant has developed a new immunotherapeutic approach for the treatment of recalcitrant bacterial biofilm-mediated infections. This new approach is based on nucleoprotein interactions that take place in the biofilm extracellular matrix. It is known that biofilm extracellular matrix is composed of a variable mix of proteins, lipids, polysaccharides and extracellular DNA (eDNA). Key components of the extracellular matrix, crucial for bacterial biofilm structural integrity are the eDNA and the bacterial DNABII family of proteins (IHF and HU). DNABII proteins bind and bend double-stranded DNA (dsDNA) with high affinity to pre-bend DNA (FIG. 1). It has been shown in vivo, that there is a vast network of interlaced eDNA strands in biofilms formed that is stabilized by DNABII proteins positioned at the vertices of bent crossed strands of eDNA. Applicant discloses here that the polypeptides of eukaryotic origin that have one or more HMG-box domain(s), such as HMGB1, can interfere with the structure of extracellular DNA scaffold inside biofilms. By competing with microbial proteins that bind to the DNA scaffold in the biofilm, these polypeptides destabilize the biofilm, which leads to destruction and removal of the biofilm by the host immune system (FIG. 2).

This new therapeutic approach is innovative since it is the first time that HMGB1 and its variants are tested for their bacterial anti-biofilm therapeutic potential. Also, HMGB1 domains and mutation variants, A box, B box, C tail, and A+B Box (FIG. 3) which harbor different anti-biofilm and anti-inflammatory properties were tested in order to determine the optimal protein fragment with the best anti-biofilm, less anti-inflammatory activity, and smallest protein fragment size. In this regard, this protein fragment would be able to treat bacterial biofilm diseases without the consequences of excessive inflammation. In addition, since release of bacteria from the biofilm renders these bacteria more susceptible to antibiotic-mediated killing this would indicate that HMGB1 treatment can potentially be used in combination with conventional treatments like antibiotics which would increase anti-biofilm efficacy and reduce the development of antimicrobial resistance.

Figure 4:
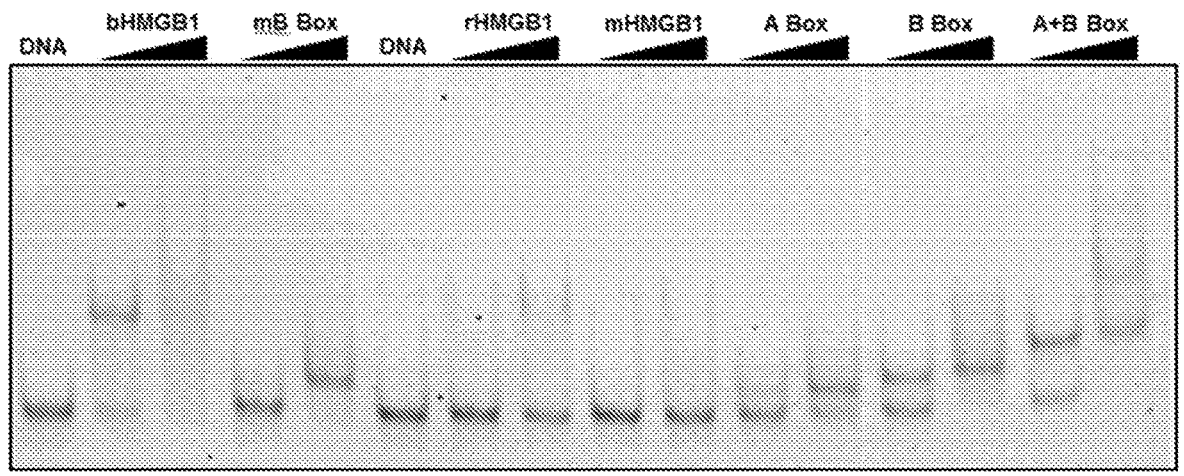
FIG. 4: HMGB1 variants maintain DNA binding abilities. Increasing concentrations (100 & 250 nM) of commercially available bovine HMGB1 (bHMGB1), B Box C106S (mB Box), rHMGB1, HMGB1 C45S (mHMGB1), A Box, B box, and A+B Box were incubated with 5' end labeled 6-carboxyfluorescein labeled Holliday Junction (HJ) DNA (20 nM) and then resolved on a 6% non-denaturing polyacrylamide gel. HMGB1 and HMGB1 variants retain DNA binding activity as illustrated by the differences HJ migration.
Figures 5A, 5B, 5C:
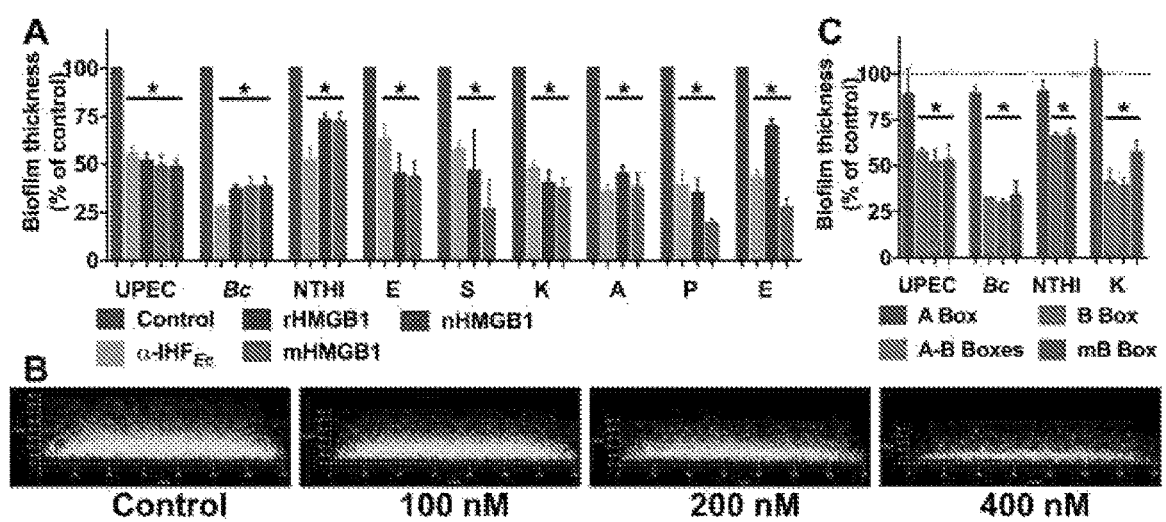
FIGS. 5A-5E: Anti-biofilm effect of HMGB1 variants on high priority bacterial pathogens. Indicated HMGB1 variants or antibodies against DNABII proteins (α-1HF$_{Ec}$ 1gG, 1 µM) were added at 24 h to the respective preformed bacterial biofilms, in vitro. After 16 h of Incubation, biofilms were stained with LIVE/DEAD®, then visualized via confocal laser scanning microscopy. Images were analyzed by COMSTAT to calculate average thickness and comparison to control was plotted.
Figures 5D, 5E:
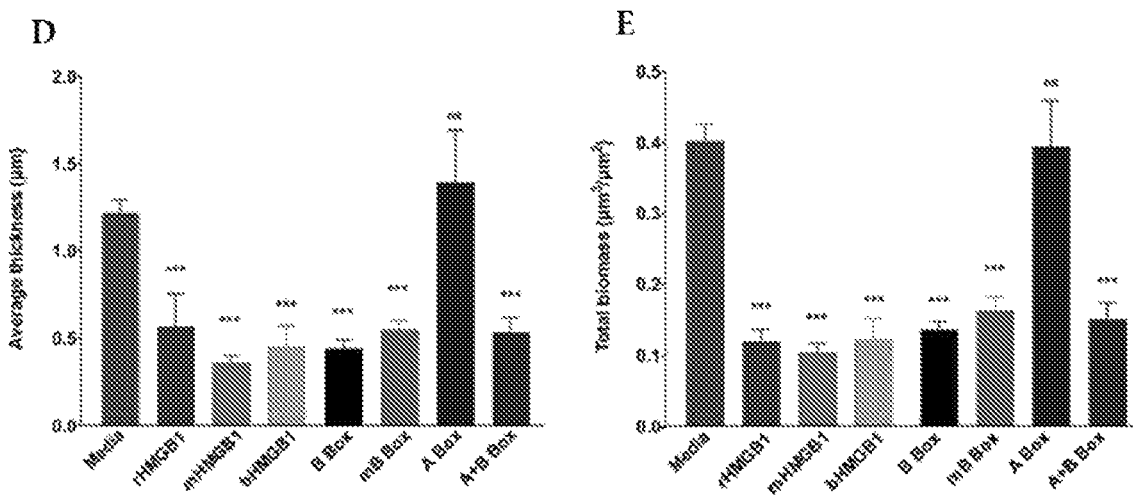

An in vitro biofilm assay was used to test the effect of HMGB1 and its variants on established bacterial biofilms. Applicant expressed, (in *E. coli*) and purified >95% human recombinant full length HMGB1 (rHMGB1; 1-215), a C45S mutated variant (mHMGB1) and the HMGB1 domains A Box (1-89), A+B Boxes (1-176), B Box (80-179), and B Box C106S (mB Box) (FIG. 3). All full length and HMGB1 variants retained DNA binding activity, which indicated that these domains were properly folded and functional (FIG. 4). To evaluate the effect of HMGB1 and its variants as well as a commercially available native bovine HMGB1 (used as a control) on established bacterial biofilms, each protein was added (at 200 nM), to pre-formed *Klebsiella pneumoniae* biofilms after 24 h of growth. After a 16 h incubation (40 h total biofilm growth), the biofilms were stained with LIVE/DEAD® and analyzed using confocal laser scanning microscopy (CLSM) and COMSTAT analysis to calculate the average thickness and total biomass of the biofilms. Full length recombinant HMGB1 was able to significantly disrupt established *K. pneumoniae* biofilms as were all truncated HMGB1 forms that contained the B Box domain (FIG. 5). The results of this study lead to a noteworthy observation that a single dose of these non-antimicrobial compounds was able to disrupt recalcitrant biofilms. In addition, the HMGB1 variants have disrupted every bacterial species tested to date, which includes Uropathogenic *E. coli*, *Burkholderia cenocepacia*, Nontypeable *Haemophilus influenzae* (FIG. 6). A single dose at this concentration released of bacteria from their protective shield makes them vulnerable to clearance by antibiotics and the immune system.

Figures 7A, 7B, 7C, 7D, 7E, 7F, 7G:
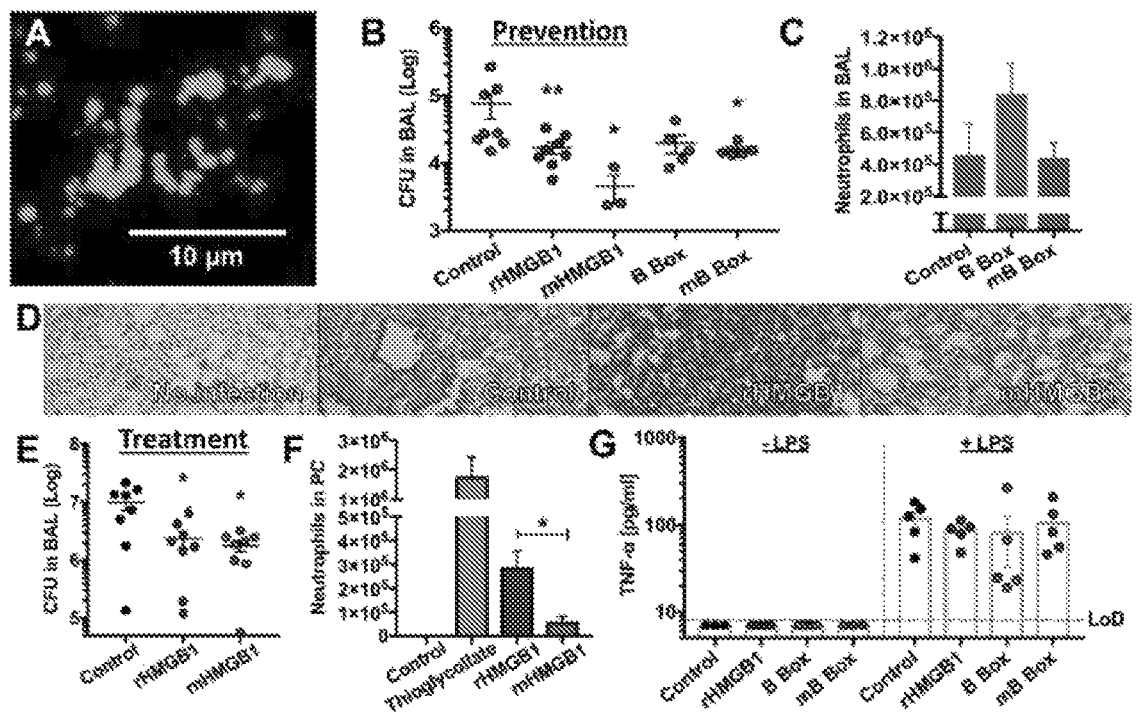
FIGS. 7A-7G: HMGB1 promotes clearance of *S. cenocepaca* from mice without inducing sepsis. C57BL/6 mice were challenged with 107 CFU intratracheally, and either simultaneously (prevention) or 24 h later (treatment) received 0.2 nmol of HMGB1 valiant.

Applicant's novel approach of using a non-antimicrobial agent like HMGB1 protein and its variants for the treatment of biofilm related infections epitomizes a radical departure from classic therapeutic concepts. Full length HMGB1 and the smallest variant tested to date with the greatest disruption activity found in vitro, B Box and the modified B Box (mB Box) where the cysteine at position 106 was mutated to a serine to abrogate its inflammatory inducing ability, were tested in vivo for biofilm disruption and inflammatory activity (FIG. 7). Utilizing an aggregate biofilm infection lung model, Applicant shows that HMGB1, B box and the modified version of each were able to prevent biofilm formation in vivo and that the modified proteins did not induce an inflammatory response (FIG. 7B & FIG. 7C).

Further applicant demonstrated that none of the HMGB1 variants induced sepsis at the doses given that are able to disrupt biofilms (FIG. 7D).
Methods
Experiment No. 1

*Klebsiella pneumoniae* (KP), a common cause of nosocomial infections was used for all BBs disruption assays. Human recombinant full length HMGB1 (rHMGB1; 1-215), a C45S mutation variant (mHMGB1) and the HMGB1 domains A Box (1-89), B Box (90-176), AB Boxes (1-176), B-linker Box (80-179), and B-linker Box C106S were expressed (in *E. coli*) and purified to >95%. To evaluate the effect of rHMGB1 and the various domains on established BBs, each protein species (200 nM) was added to preformed BBs at 24 h. At 40 h the BBs were washed, stained with LIVE/DEAD®, visualized via confocal laser scanning microscopy and images were analyzed by COMSTAT to calculate average thickness and biomass.

Exogenous rHMGB1 and its individual domains, with the exception of A Box caused a significant reduction ($p<0.05$) in average thickness (AT) and biomass (BM) of KP biofilms as compared to untreated KP biofilms (% reduction mean±SE in AT: 44%±0.33, 75%±0.04, 63%±0.1, 77%±0.03, 64%±0.08, 54%±0.15 and in BM: 61%±0.01, 80%±0.01, 68%±0.02, 67%±0.01, 73%±0.02, 56%±0.02 induced by rHMGB1, mHMGB1, B-Box, B-linker Box, AB Boxes, and B-linker Box C106S, respectively).
Experiment No. 2

HMGB1 disrupts pathogenic biofilms: To test the effect of HMGB1 on bacterial biofilms (FIG. 5), Applicant cloned (IMPACT®, NEB Ipswich, MA), expressed (in *E. coli*), and purified (heparin sepharose chromatography to >95% purity) tagless human recombinant HMGB1 (rHMGB1) and an engineered C45 S variant (mHMGB1) that mimics the reduced form of HMGB1. rHMGB1 readily forms an intramolecular disulfide bond between C23 and C45 that contributes to pro-inflammatory activity whereas mHMGB1 cannot. These HMGB1 isoforms were evaluated for ability to disrupt established biofilms (formed for 24 h prior to addition). After a 16 h exposure to a single dose of rHMGB1 (200 nM; ~25-fold greater than typical sepsis serum concentration, but not able to directly induce sepsis), biofilms formed by a wide variety of high priority species were stained with LIVE/DEAD®, analyzed using confocal laser scanning microscopy (CLSM) and COMSTAT analysis and compared to control biofilms. Applicant observed a significant reduction ($P<0.05$) in average thickness and biomass (not shown) of each biofilm (FIG. 5A). Only *E. faecium* and *S. aureus* required a higher (albeit non-bactericidal) concentration to achieve a similar result. Also shown was that a native HMGB1 purified from calf thymus (nHMGB1; Chondrex, Inc, Redmond, WA) equivalently disrupted select biofilms (UPEC, Bc, NTHI, *K. pneumoniae*) compared to rHMGB1 (FIG. 5A), which indicated that any potential differences in post-translational modification (PTMs) between nHMGB1 and rHMGB1 did not significantly impact this anti-biofilm function. Preliminary analysis of PTMs by LC-MS/MS analysis (MS Bioworks, LLC Ann Arbor, MI) indicated minimal modification of both rHMGB1 and nHMGB1 (<20% of the observed peptides had any given PTM, FIG. 1C). Progressively higher concentrations of rHMGB1 (up to 400 nM) disrupted a UPEC biofilm in a dose-dependent manner down to a monolayer (~1 µm average thickness; FIG. 5B), i.e. complete elimination of the 3D biofilm structure, which implies one can reduce the bioburden such that host immune effectors or other antimicrobial compounds can complete the eradication. Thus, while there are intrinsic differences in sensitivity among pathogens, the biofilms formed by all of the tested high priority pathogens were susceptible to a single dose of these non-antimicrobial compounds.
Experiment No. 3

Figures 8A, 8B, 8C, 8D, 8E, 8F:
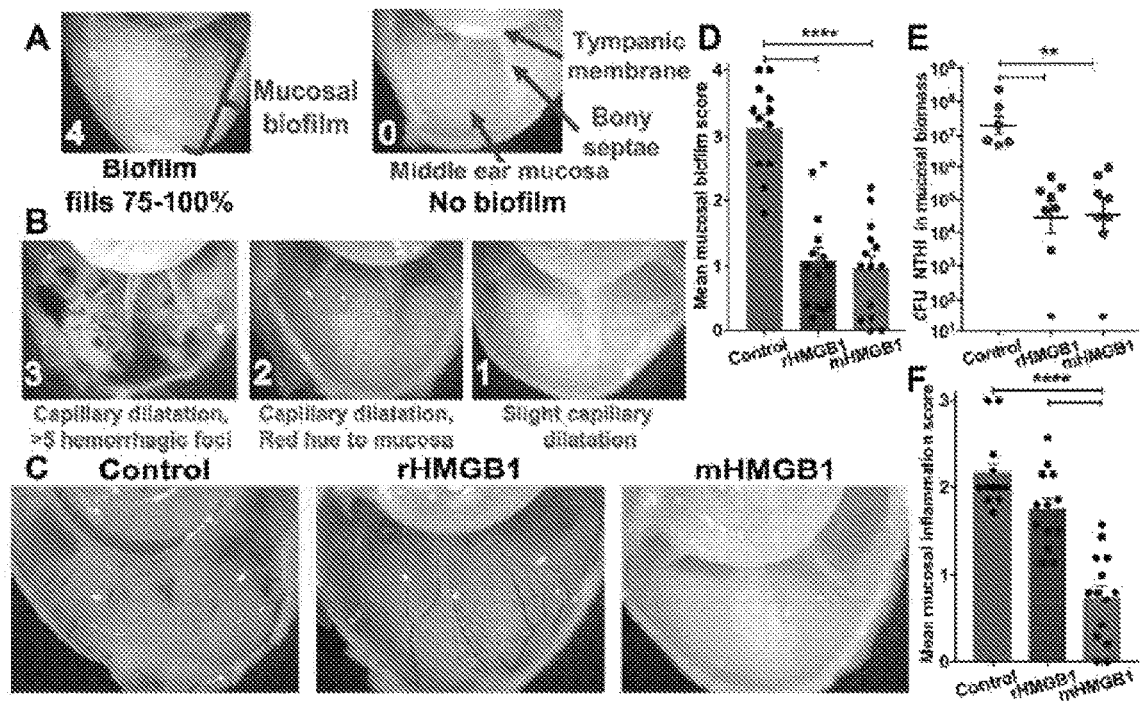
FIGS. 8A-8F: rHMGB1 and mHMGB1 promote biofilm resolution in an experimental otitis media model. Diluent, 0.2 nmol rHMGB1, or 0.2 nmol mHMGB1 were delivered directly to middle ears of chinchillas at 4 and 5 days post-challenge with NTHI. Animals were sacrificed 24 h later, middle ears were imaged (FIG. 8C, representative images) and, based on the criteria described in (FIG. 8A, biofilm) and (FIG. 8B, inflammation), blindly scored for presence of biofilm (FIG. 8D) and inflammation (FIG. 8F). CFU of NTH1 present in the mucosal biomass were quantified (FIG. 8E). Means and SEM are plotted. P<0.01, **P<0.0001. Images scoring and CFU quantification demonstrate that both rHMGB1 and mHMGB1 promoted clearance of established NTHI biofilms in vivo. Notably mHMGB1 did not induce overt inflammation.
Figure 9:
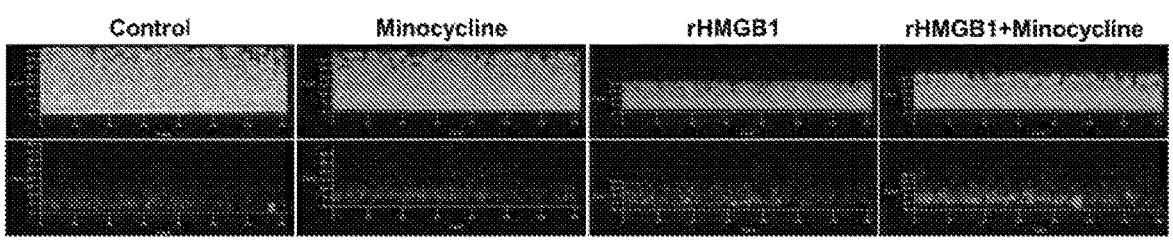
FIG. 9: HMGB1 potentiates antibiotic-mediated killing. *B. cenocepacia* biofilm was formed for 24 h prior to addition of minocycline (1 μg/ml), rHMGB1 (200 nM), or rHMGB1 (200 nM)+minocycline (1 μg/ml) for an additional 16 h. Biofilms were stained with LIVE/DEAD® and imaged via CLSM. Live cells are indicated in green and dead cells in red. Note the increase in dead cells only in the presence of both HMGB1 and minocycline.
Figures 10A, 10B:
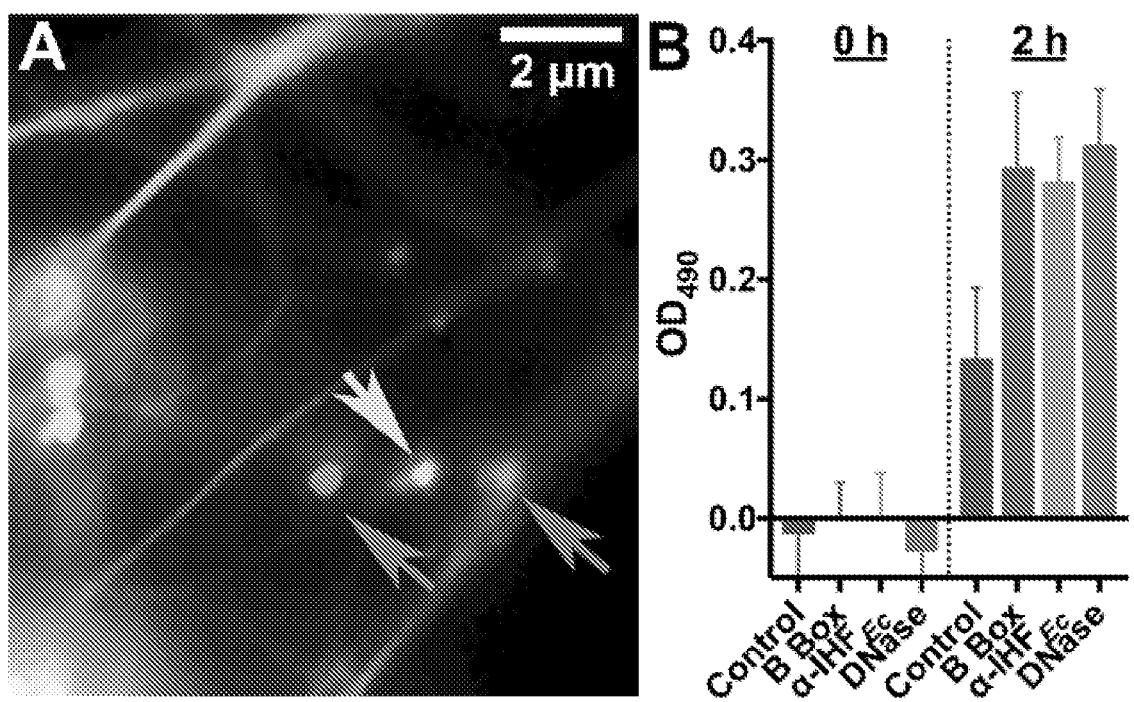
FIGS. 10A-10B: HMGB1 In specimens from biofilm-associated diseases.

HMGB1 domain structure and anti-biofilm activity: Applicant then produced recombinant HMGB1 truncation variants, of 1) the A Box, a self-contained DNA-binding domain (residues 1-89); 2) an A-B Boxes construct (lacks the C tail; residues 1-185); and 3) the B Box (residues 80 to 176, FIGS. 1A and 1C). Addition of A Box to established biofilms (UPEC, Bc, NTHI, and *K. pneumoniae*) had no significant effect on measured biofilm parameters (FIG. 5C). In contrast, the A-B Boxes and the 97 amino acid (AA) B Box retained full anti-biofilm activity (FIG. 5C). Since only the B Box can modulate DNA bending, without being bound by theory, it was hypothesized that HMGB1 disrupts biofilms at least in part via DNA-binding/bending. As the B Box is reported to contain pro-inflammatory activity, mediated primarily through interactions with TLR4-MD2 that are dependent on residue C106, Applicant created a modified B Box variant (mB Box) with a C106S mutation (FIGS. 1A and 1C). The mB Box variant equivalently disrupted bacterial biofilms (UPEC, NTHI, Bc, *K. pneumoniae*) in vitro compared to B Box (FIG. 5C).
Experiment No. 4 rHMGB1 and mHMGB1 disrupt biofilms in two distinct animal models but the inflammatory response is strongly attenuated with Cys to Ser mutations: Applicant tested both rHMGB1 and mHMGB1 for their ability to treat middle ear infection and the corresponding inflammatory response using a well-established chinchilla model of experimental OM due to NTHI49,67,68 wherein adhered mucosal biofilm formation plays a key role in pathogenesis (FIG. 8A). The middle ear of mixed sex, outbred adult chinchillas were inoculated with 1000 CFU NTHI by transbullar injection. At days 4 and 5 post-challenge, at which time there is abundant biofilm present in the middle ear space, 5 (0.2 nmol) of rHMGB1, mHMGB1, or diluent was delivered directly to the middle ear (2 total treatments). On day 6, animals were sacrificed and middle ears were imaged and blindly scored for biofilm that remained (FIG. 8A) and mucosal inflammation (FIG. 8B). Animals treated with diluent possessed a thick mucosal biofilm that masked bony septate (FIGS. 8C and 8D). In stark contrast, residual mucosal biofilms were drastically reduced in animals treated with rHMGB1 or mHMGB1, with a ~1000 fold reduction in CFU (FIG. 8E). These results are especially noteworthy, as biofilms formed by NTHI in vitro were not as responsive to HMGB1 addition as other bacterial species tested (FIG. 5). Middle ear fluids (MEFs) collected from rHMGB1-treated animals had increased pro-inflammatory cytokines [IL-1β (3-fold), IL-17A (2-fold)], compared to both mHMGB1 and diluent treated animals (data not shown), consistent with rHMGB1 enhanced visible inflammation of the middle ear mucosa (FIGS. 8C and 8F). In contrast, MEFs from mHMGB1-treated animals had increased anti-inflammatory cytokines [IL-4 (2-fold), IL-10 (5-fold)] (data not shown), which corresponded with reduced mucosal inflammation (FIGS. 8C and 8F). Therefore, mHMGB1 efficiently facilitated clearance of NTHI biofilms in vivo and did so without triggering pro-inflammatory signals. Next, Applicant determined whether rHMGB1 or mHMGB1 could prevent or aggregate biofilm development. For prevention, adult C57BL/6 mice were challenged with $10^7$ CFU of Bc intratracheally (i.t.), and 0.2 nmol of rHMGB1 or mHMGB1 was added simultaneously. After 18 h, mice were euthanized, and bronchoalveolar lavage (BAL) and lungs were collected. Bc formed aggregates that were readily visible in lung sections probed with Bc antibody (FIG. 7A). Tissue was homogenized and CFUs were enumerated. Mice for which rHMGB1 or mHMGB1 were administered contained significantly fewer Bc in BAL (FIG. 7B) and lung tissue (data not shown; P<0.05) compared to control mice, which suggested that HMGB1 inhibited biofilm formation in the murine airways and that this process facilitated bacterial clearance. Preliminary results of treatment with the B Box and the mB Box derivative indicated that these 97 AA polypeptides inhibit biofilm development in vivo (decreased CFU in BAL, FIG. 7B) and that the C106S mutation abrogates pro-inflammatory activity, a 2-fold reduction compared to B Box, (FIG. 7C). This same animal model was then used to investigate lung damage 72 h post-challenge with Bc and administration of rHMGB1 or mHMGB1. Lungs were collected and tissue was fixed, embedded in paraffin, sectioned, and stained with Haematoxylin and Eosin (H&E). Lungs from mice treated with mHMGB1 more closely resembled uninfected mouse lungs, whereas severe inflammation and an increased neutrophil response occurred in the rHMGB1-treated mice (FIG. 7D), which indicates that mHMGB1 retained anti-biofilm activity without the pro-inflammatory activity of rHMGB1. Next, Applicant assessed the ability of rHMGB1 and mHMGB1 to treat established Bc infection. Mice were challenged as above and 0.2 nmol rHMGB1 or mHMGB1 was administered 24 h later. 48 h after treatment, mice were euthanized and BAL and lungs were collected and processed as above. Mice treated with rHMGB1 or mHMGB1 had significantly fewer Bc in their lungs (FIG. 7E), while mHMGB1 treatment induced less neutrophil and inflammatory monocyte recruitment to the lung ($P<0.05$, data not shown). Collectively, these data show that mHMGB1 and mB Box did not enhance the inflammatory response, but rather inhibited aggregate biofilm formation, bacterial uptake, and clearance. To further validate the reduced pro-inflammatory activity of mHMGB1, Applicant used an in vivo model of chemotaxis to determine relative ability to recruit neutrophils70,71. C57BL/6 mice were intraperitoneally (i.p.) injected with 0.2 nmol of either mHMGB1 or rHMGB1 or 1 ml of 4% thioglycollate (positive control; inducer of neutrophil recruitment). After 4 h, mice were euthanized and peritoneal lavage was performed. Cells were stained with anti-CD45, anti-CD11b, and anti-Ly6G antibodies, and total neutrophils were quantified by Fluorescence-Activated Cell Sorting (FACS). rHMGB1 induced neutrophil recruitment to the peritoneal cavity, whereas mHMGB1 did not (FIG. 7F).

Experiment No: 5

HMGB1 variants do not induce sepsis at doses required to treat biofilm disease: Despite the fact that HMGB1 variants with Cys to Ser mutations (mHMGB1, mB Box) did not induce pro-inflammatory sequelae with a single dose of HMGB1 and B Box, but still showed potent anti-biofilm activity, Applicant nevertheless rigorously investigated whether administration of our HMGB1 variants would elicit sepsis in the presence or absence of LPS. Applicant injected naïve mice or mice primed with a non-lethal dose of LPS (5 mg/kg) i.p. with 0.2 nmol (same amount that exhibited therapeutic benefit in treatment of in vivo biofilms) of endotoxin free rHMGB1, B Box, or mB Box [purified with High Capacity Endotoxin Removal Resin (Pierce, Inc) and verified by endotoxin quantitation (Genscript) to contain <300 pg endotoxin/μg protein]. Mice were monitored for 24 h for signs of sepsis, then serum TNF-alpha (TNF-α) levels were measured by ELISA as a surrogate for sepsis induction. No mice displayed signs of sepsis that required euthanasia prior to the study endpoint. While LPS alone induced over 100 pg/ml of TNF neither rHMGB1, B Box, nor mB Box elicited detectable TNF on their own, and none induced additional pro-inflammatory signaling when administered to LPS-primed mice (FIG. 7G). It has been reported, that compared to our doses, >450-fold for B Box alone, or 4 doses of 2-fold greater amounts of rHMGB1 in 40 h with lipopolysaccharide (LPS)-primed mice20 are required to induce sepsis. In addition, these endotoxin-free polypeptides were tested for anti-biofilm activity in vitro as described above and found to maintain full function against UPEC and Bc biofilms (data not shown). Therefore, the variants tested here do not induce sepsis at potent therapeutic doses.

Experiment No. 6

Biofilm disruption by HMGB1 sensitizes released bacteria to antibiotics: 200 nM HMGB1 was added to Bc biofilms as above, 1 μg/ml minocycline, or both. Use of LIVE/DEAD® stain revealed synergistic bacterial killing (FIG. 9), which indicates that HMGB1 treatment can be used in combination therapy that could both increase antimicrobial efficacy and reduce development of antimicrobial resistance.

Experiment No. 7

HMGB1 and DNABII protein(s) are present within biofilms formed in vivo: Applicant previously demonstrated that in biofilms formed by NTHI in an experimental model of OM, bacterial DNABII proteins were positioned at the vertices of crossed strands of eDNA. To determine the relative presence and spatial distribution of HMGB1 within an NTHI biofilm formed in vivo, unfixed biofilms recovered from the chinchilla middle ear were probed with both HMGB1 as well as DNABII antibodies. eDNA was stained with DAPI (white). HMGB1 labeled with distinct periodicity along the length of dsDNA strands and in close proximity to, but not co-localized with, the labeled DNABII protein, which was detected (as expected) at crossed strands of eDNA (FIG. 10A). Notably, HMGB1 was not observed at vertices. These data suggest that HMGB1 can be integrated within the EPS but does not simultaneously co-occupy the same eDNA site (vertices) as the DNABII proteins, which supports the hypothesis that HMGB1 competes with DNABII proteins at the eDNA vertices to destabilize the EPS. These data also suggest that DNABII and HMGB1 proteins do not interact productively as they do not co-localize and further, shows that HMGB1 likely functions solely through DNA-binding/bending.

Experiment No. 8

HMGB1 disrupts biofilms present in clinical specimens: Biofilms at chronic disease sites (e.g. CF lung), consist of multiple species and by nature are difficult to eradicate. It has been shown that anti-DNABII antibodies to disrupt biofilms present in CF sputum. Suspensions of CF sputum in PBS that contain 1 M B box and incubated at 37° C. for 2 h disrupted sputum effectively and to the same degree as addition of high concentrations of Pulmozyme® (a therapeutic DNase used as a mucolytic in CF patients) or anti-DNABII (FIG. 10B). These data indicate biofilms formed at chronic infection sites have a conserved eDNA-dependent architecture that is susceptible to HMGB1 and validates HMGB1 as a host defense against biofilms.

Experiment No. 9

A number of oral bacteria (e.g., *Aggregatibacter actinomycetemcomitans, Porphyromonas gingivalis*) have been implicated in the pathogenesis of inflammatory diseases such as periodontitis and peri-implantitis, which destroy alveolar bone and gingiva. Investigations of the pathogenesis of these bacteria are hampered by lack of effective animal models. One of the challenges of investigating the pathogenicity of specific bacteria is the difficulty of establishing a biofilm when exogenous bacteria are introduced into the oral cavity of animals. Though animal models of periodontitis have been developed, cultivable bacteria are rarely recovered from the oral cavity of inoculated animals. Developing an effective animal model which can assess the pathogenicity of specific bacteria will greatly aid in elucidating their pathogenic mechanisms. This example provides a model to test the disclosed polypeptides and compositions and their effechinis in treating oral disease.

The surface of machined titanium dental implants (1.2× 4.5 mm) is modified by grit blasting with A103 (100 µm) and HCl etching (pH 7.8 for 20 min at 80° C.). Machined and nano-textured implants were incubated in TSB medium inoculated with D7S clinical strain of *Aggregatibacter actinomycetemcomitans* (Aa) for 1 to 3 days at 37° C. The bacterial biofilm on the implants are analyzed by SEM, as well as by confocal laser scanning microscopy following staining with LIVE/DEAD® BacLight™. Implants with and without established Aa biofilm are transmucosally placed into the alveolar bone of female rats between premolar and incisor region of the maxillae. To detect the presence of Aa biofilm on the implants placed in vivo, bacterial samples are collected from saliva and the oral surfaces of implants after 2 days. Aa can be detected by culture, as well as by PCR analysis. Micro-CT and histological analysis of peri-implant bone and mucosal tissues can be performed six weeks after implantation. The polypeptides and compositions and attached with the surface as described herein and biofilm and bacterial growth is assayed.

Experiment No. 10

This experiment provides a mouse model for pre-clinical testing of interfering agents to treat lyme disease. See Dresser et al. Pathogens 5(12)e1000680, Epub 2009 Dec. 4. Lyme disease is the most common tick-borne disease in the United States. By definition, these endemic areas are expanding as populations continue to move from cities to suburban and rural areas and whitetail deer (which carry the tick species *Ixodes*) increasingly roam these areas. Lyme disease is caused by the microorganism *Borrelia burgdorferi*, a spirochete. *B. burgdorferi* is transmitted via the bite of the *Ixodes* tick and subsequently disseminates, via the bloodstream, to other tissues and organs.

In this animal model, C3H/HeN mice are injected with spirochetes via dorsal subcutaneous and intraperitoneal injection, or via intravenous injection. Blood and biopsy specimens are recovered at approximately 7 days post infection for evaluation of microbial burden and assessment of pathology in tissues and organs. The methods and compositions of this invention are contemplated to develop both therapeutic as well as preventative strategies for reduction and/or elimination of the resulting *B. burgdorferi* biofilms which form subsequent to challenge and are believed to contribute to both the pathogenesis and chronic nature of the disease.

Experiment No. 11

This experiment provides a porcine model for pre-clinical testing of the desdones polypeptides and compositions to treat cystic fibrosis. See Stoltz et al. (2010) Science Translational Medicine 2(29): 29ra31. Cystic fibrosis is an autosomal recessive disease due to mutations in a gene that encodes the CF transmembrane conductance regulator (called CFTR) anion channel. In this model, pigs which have been specifically bred to carry a defect in the genes called "CFTR" and called CF pigs spontaneously develop hallmark features of CF lung disease that includes infection of the lower airway by multiple bacterial species. The pigs can be administered the composition to deliver polypeptides to the lungs of these animals by nebulization to assess the amelioration of the signs of disease and associated pathologies.

Experiment No. 12

Applicants also provide a pre-clinical model for tuberculosis (TB). See Ordway et al. (2010) Anti. Agents and Chemotherapy 54:1820. In this animal model, SPF guinea pigs are maintained in a barrier colony and infected via aerosolized spray to deliver ~20 cfu of *M. tuberculosis* strain Erdman K01 bacilli into their lungs. Animals are sacrificed with determination of bacterial load and recovery of tissues for histopathological assessment on days 25, 50, 75, 100, 125 and 150 days post-challenge. Unlike mice which do not develop classic signs of TB, guinea pigs challenged in this manner develop well-organized granulomas with central necrosis, a hallmark of human disease. Further, like humans, guinea pigs develop severe pyogranulomatous and necrotizing lymphadenitis of the draining lymph nodes as part of the primary lesion complex. Use of this model will provide a pre-clinical screen to confirm and identify therapeutic as well as preventative strategies for reduction and/or elimination of the resulting *M. tuberculosis* biofilms which have been observed to form in the lungs of these animals subsequent to challenge and are believed to contribute to both the pathogenesis and chronicity of the disease.

Experiment No. 13

Multiple animal models of catheter/indwelling device biofilm infections are known. See Otto (2009) Nature Reviews Microbiology, 7:555. While typically considered normal skin flora, the microbe *Staphylococcus epidermidis* has become what many regard as a key opportunistic pathogen, ranking first among causative agents of nosocomial infections. Primarily, this bacterium is responsible for the majority of infections that develop on indwelling medical devices which are contaminated by this common skin colonizer during device insertion. While not typically life-threatening, the difficulty associated with treatment of these biofilm infections, combined with their frequency, makes them a serious public health burden. There are several animal models of catheter-associated *S. epidermidis* infections including rabbits, mice, guinea pigs and rats all of which are used to study the molecular mechanisms of pathogenesis and which lend themselves to studies of prevention and/or therapeutics. Rat jugular vein catheters have been used to evaluate therapies that interfere with E. *Faecalis, S. aureus* and *S. epidermidis* biofilm formation. Biofilm reduction is often measured three ways—(i) sonicate catheter and calculate CFUs, (ii) cut slices of catheter or simply lay on a plate and score, or (iii) the biofilm can be stained with crystal violet or another dye, eluted, and OD measured as a proxy for CFUs.

CONCLUSION

Full length recombinant HMGB1 was able to significantly disrupt established biofilms as were all truncated HMGB1 forms containing the B Box domain.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

SEQUENCE LISTING

SEQ ID NO: 1 and 2—Wild-Type HMGB1 (Murine and Human)
```
  1 MGKGDPKKPR RKMSSYAFFV QTCREEHKKK
    HPDASVNFSE FSKKCSERWK TMSAKEKGKF
 61 EDMAKADKAR YEREMKTYIP PKGETKKKFK
    DPNAPKRPPS AFFLFCSEYR PKIKGEHPGL
121 SIGDVAKKLG EMWNNTAADD KQPYEKKAEK
    LKEKYEKDIA AYRAKGKPDA AKKGVVKAEK
181 SKKKKEEEEG EEDEEDEEEE EDEEDEDEEE
    DDDDE (murine)
  1 MGKGDPKKPR GKMSSYAFFV QTCREEHKKK
    HPDASVNFSE FSKKCSERWK TMSAKEKGKF
 61 EDMAKADKAR YEREMKTYIP PKGETKKKFK
    DPNAPKRPPS AFFLFCSEYR PKIKGEHPGL
121 SIGDVAKKLG EMWNNTAADD KQPYEKKAAK
    LKEKYEKDIA AYRAKGKPDA AKKGVVKAEK
181 SKKKKEEEED EEDEEDEEEE EDEEDEDEEE
    DDDDE
```
(Human, reproduced from GenBank Accession No. CAE48262.1).

HMGB1 is a small protein of 215 amino acid protein (of approx 30 Kda) composed of 3 domains: two positively charged domains the A and B box each one comprising of 80 amino acids and a negatively charged carboxyl terminus the acidic C tail which consists of approximately 30 consecutive aspartate and glutamate residues.

Bolded amino acids (amino acids 1-70) depict the A Box domain.

The italiced amino acids (about amino acids 88-164) depict the B Box domain.

The underlined amino acids (amino acids 186-215) depict the C-tail domain.

Mutated versions of HMGB1 are shown in FIG. 1 and FIG. 3 with the amino acid substitutions.

SEQ ID NO: 3 and 4
Wild-type Murine HMGB1 B Box: MW=9735.2; 87 aa
KDPNAPKRPPSAFFLFCSEYRPKIKGEHPGLSIGD-VAKKLGEMWNNTAADDKQPYEKK
AEKLKEKYEKDIAAYRAKGKPDAAKKGVV
Wild-Type Human HMGB1 B Box: 87 aa
KDPNAPKRPPSAFFLFCSEYRPKIKGEHPGLSIGD-VAKKLGEMWNNTAADDKQPYEKK AAK-LKEKYEKDIAAYRAKGKPDAAKKGVV SEQ ID NO: 5 and 6
Murine Mutated HMGB1 B Box: MW=9735.2; 87 aa
KDPNAPKRPPSAFFLFSSEYRPKIKGEHPGLSIGD-VAKKLGEMWNNTAADDKQPYEKKA
EKLKEKYEKDIAAYRAKGKPDAAKKGVV
Human Mutated HMGB1 B Box: 87 Aa
KDPNAPKRPPSAFFLFSSEYRPKIKGEHPGLSIGD-VAKKLGEMWNNTAADDKQPYEKKA
AKLKEKYEKDIAAYRAKGKPDAAKKGVV The Cysteine (C) has been mutated to Serine (S) (bolded text).

SEQ ID NO: 7 and 8
Wild-Type Murine HMGB1 A+B Box: MW=20261.42; 176 aa
MGKGDPKKPRRKMSSYAFFVQTCREEHKKKHP-DASVNFSEFSKKCSERWKTMSAKEK GKFED-MAKADKARYER-
EMKTYIPPKGETKKKFKDPNAPKRPPSAFFLFC
SEYRPKIKGE HPGLSIGDVAKKLGEMWNN-TAADDKQPYEKKAEKLKEKYEKDIAAY-RAKGKPDAAK KGVV
Wild-Type Human HMGB1 A+B Box: 176 aa
MGKGDPKKPRGKMSSYAFFVQTCREEHKKKHP-DASVNFSEFSKKCSERWKTMSAKEK GKFED-MAKADKARYER-
EMKTYIPPKGETKKKFKDPNAPKRPPSAFFLFC
SEYRPKIKGE HPGLSIGDVAKKLGEMWNN-TAADDKQPYEKKAAKLKEKYEKDIAAY-RAKGKPDAAK KGVV The Cysteine (C) has been mutated to Serine (S) (bolded text).

SEQ ID NO: 9 and 10
Wild-Type Murine HMGB1 B Box+N-Linker (Underlined): MW=10876.6; 97 aa
PPKGETKKKFKDPNAPKRPPSAFFLFCSEYRP-KIKGEHPGLSIGDVAKKLGEMWNNTAA
DDKQPYEKKAEKLKEKYEKDIAAYRAKGKP-DAAKKGVV
Wild-Type Human HMGB1 B Box+N-Linker (Underlined): 97 aa
PPKGETKKKFKDPNAPKRPPSAFFLFCSEYRP-KIKGEHPGLSIGDVAKKLGEMWNNTAA
DDKQPYEKKAAKLKEKYEKDIAAYRAKGKP-DAAKKGVV SEQ ID NO: 11 and 12
Mutated HMGB1 B Box+N-Linker (Underlined): MW=10876.6; 97 aa
PPKGETKKKFKDPNAPKRPPSAFFLFSSEYRP-KIKGEHPGLSIGDVAKKLGEMWNNTAA
DDKQPYEKKAEKLKEKYEKDIAAYRAKGKP-DAAKKGVV
Human HMGB1 B Box+N-Linker (Underlined): 97 aa
PPKGETKKKFKDPNAPKRPPSAFFLFSSEYRP-KIKGEHPGLSIGDVAKKLGEMWNNTAA
DDKQPYEKKAAKLKEKYEKDIAAYRAKGKP-DAAKKGVV

What is claimed is:

1. An isolated B Box polypeptide consisting of the amino acid sequence as shown in SEQ ID NO: 12.

2. The isolated B Box polypeptide of claim 1, wherein the isolated B Box polypeptide is chemically synthesized.

3. A composition comprising a carrier and the isolated polypeptide of claim 1.

4. A kit comprising the isolated polypeptide of claim 1 and instructions for use.

5. An isolated AB Box polypeptide consisting of the amino acid sequence as shown in SEQ ID NO: 8, wherein the amino acid corresponding to C106 has a C106S mutation, and wherein the AB polypeptide is chemically synthesized.

6. The isolated AB Box polypeptide of claim 5, comprising one or more amino acid mutations at an amino acid position selected from K12, C23, C45, or K114.

7. A method for inhibiting, competing or titrating the binding of a DNABII polypeptide or protein to a microbial DNA, comprising contacting the DNABII polypeptide or protein or the microbial DNA with the polypeptide of claim 1, thereby inhibiting, competing or titrating the binding of the DNABII protein or polypeptide to the microbial DNA.

8. A method for inhibiting, preventing or breaking down a microbial biofilm, comprising contacting the biofilm with the polypeptide of claim 1, thereby inhibiting, preventing or breaking down the microbial biofilm.

9. The method of claim 8, wherein the biofilm is produced by an organism selected from the group of uropathogenic *Escherichia coli* (UPEC), *Klebsiella pneumonia, Burkholderia cenocepacia, S. epidermidis, Streptococcus agalactiae, Neisseria meningitidis, Treponemes denticola, Treponemes pallidum, Burkholderia cepacia, Burkholderia pseudomallei, Haemophilus influenzae* (nontypeable) (NTHI), *Moraxella catarrhalis, Streptococcus pneumoniae, Streptococcus pyogenes, Mycobacterium tuberculosis* or an ESKAPE pathogen.

10. A method of one or more of the following: (a) inhibiting, preventing or breaking down a biofilm in a subject, (b) inhibiting, preventing or treating a microbial infection that produces a biofilm in a subject, (c) disrupting a biofilm and clearance thereof that does not enhance or induce an inflammatory response in a subject in need thereof, or (d) treating an infection or disorder incident to the presence of a biofilm in a subject in need thereof, the method comprising administering to the subject an effective amount of the polypeptide of claim 1, thereby (a') inhibiting, preventing or breaking down the microbial biofilm, (b') inhibiting, preventing or treating a microbial infection that produces the biofilm in the subject, (c') disrupting the biofilm and clearance thereof that does not enhance or induce an inflammatory response, or (d') treating the infection or disorder incident to the presence of a biofilm in the subject, respectively.

11. The method of claim 10, further comprising administering an antimicrobial.

* * * * *